(12) United States Patent
Smith et al.

(10) Patent No.: US 7,081,135 B2
(45) Date of Patent: Jul. 25, 2006

(54) MASTOPEXY STABILIZATION APPARATUS AND METHOD

(76) Inventors: Lane Fielding Smith, 3627 South 100 West, Bountiful, UT (US) 84010; Evan Farr Smith, 3265 West 8410 South, West Jordan, UT (US) 84088

( * ) Notice: Subject to any disclaimer, the term of this patent is extended or adjusted under 35 U.S.C. 154(b) by 0 days.

(21) Appl. No.: 10/771,776

(22) Filed: Feb. 4, 2004

(65) Prior Publication Data
US 2004/0249457 A1 Dec. 9, 2004

Related U.S. Application Data

(60) Provisional application No. 60/477,100, filed on Jun. 9, 2003.

(51) Int. Cl.
A61F 2/12 (2006.01)
A61B 17/08 (2006.01)

(52) U.S. Cl. ............... 623/8; 606/151; 606/153; 623/11.11

(58) Field of Classification Search ............ 623/11.11, 623/7, 8, 5.15, 10, 14.13, 23.64, 23.65, 23.67; 606/151, 153, 191, 195
See application file for complete search history.

(56) References Cited

U.S. PATENT DOCUMENTS

| | | | |
|---|---|---|---|
| 4,047,523 A | 9/1977 | Hall | 128/69 |
| 4,095,295 A | 6/1978 | Lake | 3/36 |
| 4,205,401 A | 6/1980 | Frisch | 3/36 |
| 4,205,681 A | 6/1980 | Nestor et al. | 128/321 |
| 4,253,201 A * | 3/1981 | Ross et al. | 623/8 |
| 4,264,990 A * | 5/1981 | Hamas | 623/8 |
| 4,298,997 A | 11/1981 | Rybka | 3/36 |
| 4,507,810 A | 4/1985 | Bartholdson | 3/36 |
| 4,713,073 A | 12/1987 | Reinmüller | 623/8 |
| 4,769,036 A * | 9/1988 | Modir | 623/8 |
| 4,773,909 A | 9/1988 | Chaglassian | 623/8 |
| 4,932,966 A * | 6/1990 | Christie et al. | 623/6.13 |
| 4,950,292 A * | 8/1990 | Audretsch | 623/8 |
| 4,955,909 A | 9/1990 | Ersek et al. | 623/11 |
| 4,969,898 A * | 11/1990 | Calogero | 623/8 |
| 5,236,454 A | 8/1993 | Miller | 623/8 |
| 5,246,454 A | 9/1993 | Peterson | 623/8 |
| 5,352,307 A | 10/1994 | Wild | 156/66 |
| 5,391,203 A | 2/1995 | Bartlett et al. | 623/8 |
| 5,500,017 A | 3/1996 | Bretz et al. | 623/8 |
| 5,534,023 A | 7/1996 | Henley | 623/8 |
| 5,545,217 A | 8/1996 | Offray et al. | 623/8 |

(Continued)

OTHER PUBLICATIONS

*Surgical Needles*, T.CAD International, USA, 1997-2003, http://www.tcadinternational.com/SurgicalNeedles.html, Oct. 2, 2003, pp. 1-2.

(Continued)

*Primary Examiner*—David J. Isabella
(74) *Attorney, Agent, or Firm*—Pate, Pierce & Baird

(57) ABSTRACT

An apparatus and method for mastopexy surgeries correcting a ptosis condition caused by tissue stretching, in the breast as a result of pregnancy, time, aging, and the effects of gravity and athletic activity provide an implant having homogeneously formed connectors extending from inside an implant wall for anchoring to the chest wall or chest muscles of a patient. Embedded reinforcements and anchoring tabs or sutures may be readily oriented along a rib or other defining physiological location in order to provide immediate, permanent, and symmetric installation of implants in a mastopexy reconstruction.

21 Claims, 25 Drawing Sheets

U.S. PATENT DOCUMENTS

| | | | | |
|---|---|---|---|---|
| 5,653,754 | A | * | 8/1997 | Nakajima et al. ............ 623/4.1 |
| 5,658,328 | A | | 8/1997 | Johnson .......................... 623/8 |
| 5,676,161 | A | | 10/1997 | Breiner ....................... 128/898 |
| 5,676,698 | A | | 10/1997 | Janzen et al. .................. 623/8 |
| 5,693,164 | A | | 12/1997 | Chang .......................... 156/152 |
| 5,843,189 | A | | 12/1998 | Perouse ......................... 623/8 |
| 5,922,024 | A | | 7/1999 | Janzen et al. .................. 623/8 |
| 5,935,164 | A | | 8/1999 | Iversen .......................... 623/8 |
| 5,964,803 | A | | 10/1999 | Iversen et al. ................. 623/8 |
| 6,066,856 | A | * | 5/2000 | Fishman ................. 250/519.1 |
| 6,074,420 | A | | 6/2000 | Eaton ............................. 623/7 |
| 6,099,565 | A | | 8/2000 | Sakura, Jr. ..................... 623/8 |
| 6,146,418 | A | | 11/2000 | Berman ......................... 623/8 |
| 6,203,570 | B1 | * | 3/2001 | Baeke ............................ 623/8 |
| 6,602,452 | B1 | | 8/2003 | Schuessler ................. 264/102 |
| 6,746,458 | B1 | * | 6/2004 | Cloud ........................ 606/151 |

OTHER PUBLICATIONS

*Stainless Steel reusable Surgical Needles*, Spectrum, Surgical Instruments, Repairs, Instrument Accessories, http://www.spectrumsurgical.com/images/needle/needles1.gif, Oct. 2, 2003, p. 1.

*Sutures*, Orthoteers, http://www.orthoteers.co.uk/Nrujp-ij331m/Orthsutures.htm, Oct. 2, 2003, pp. 1-3.

*Home: Learn About Procedures: Procedures*, American Society of Plastic Surgeons, http://www.plasticsurgery.org/public_education/procedures/Mastopexy.cfm, Sep. 18, 2003, pp. 1-3.

*Breast implant filler material*, Young, V.L., Washington University, St. Louis, USA, http://users.unimi.it/~chplast/bit/151.html, Oct. 7, 2003, p. 1.

* cited by examiner

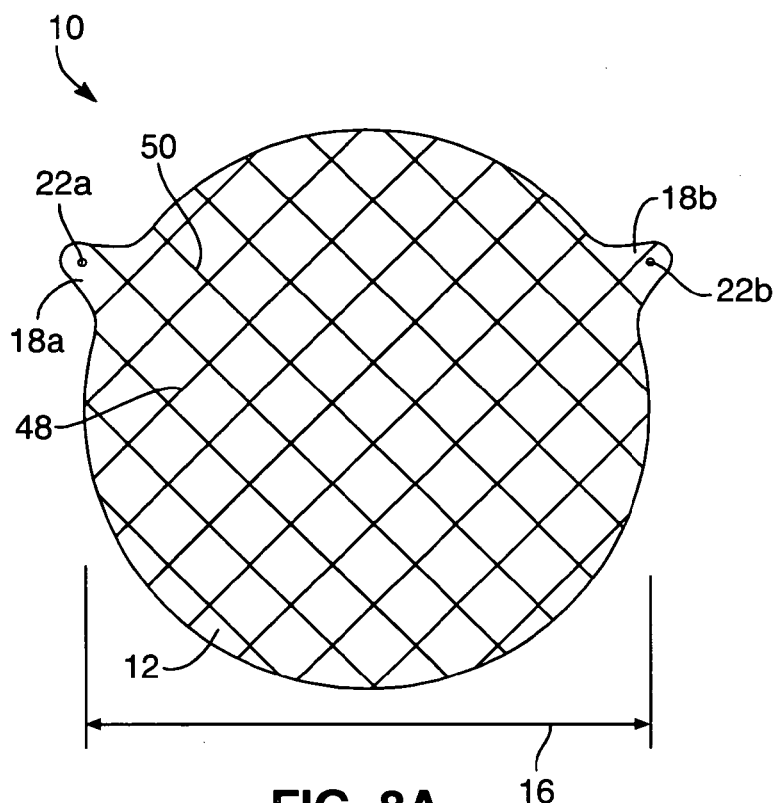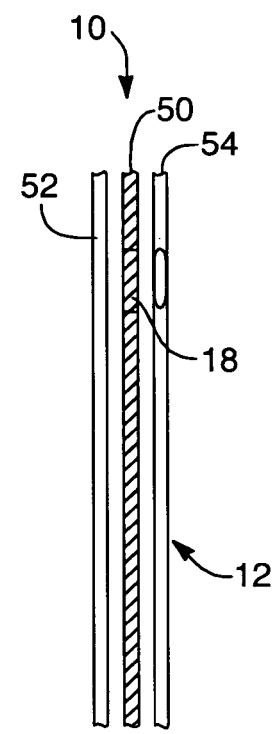
FIG. 8A  FIG. 9A
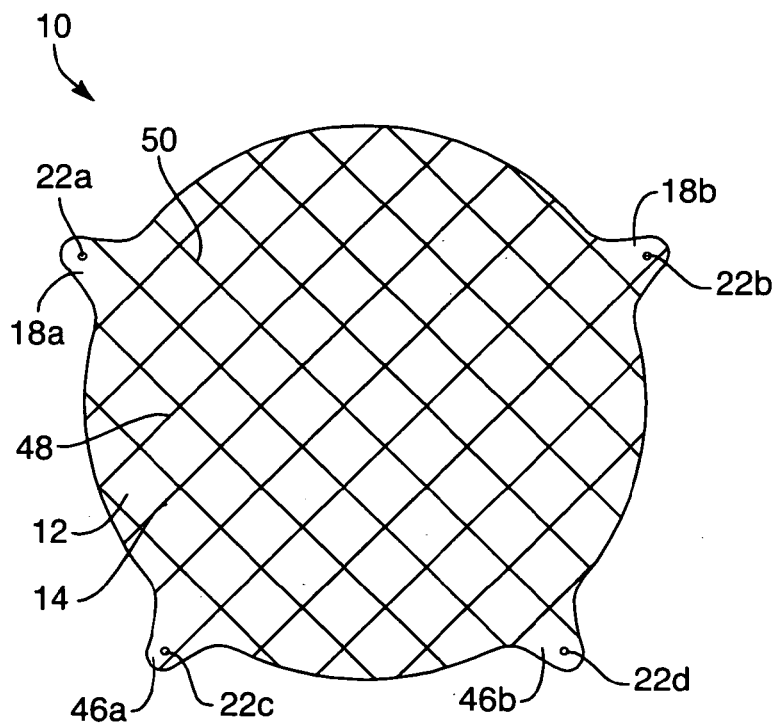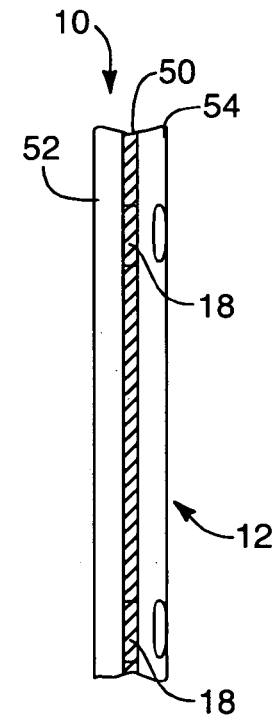
FIG. 8B  FIG. 9B

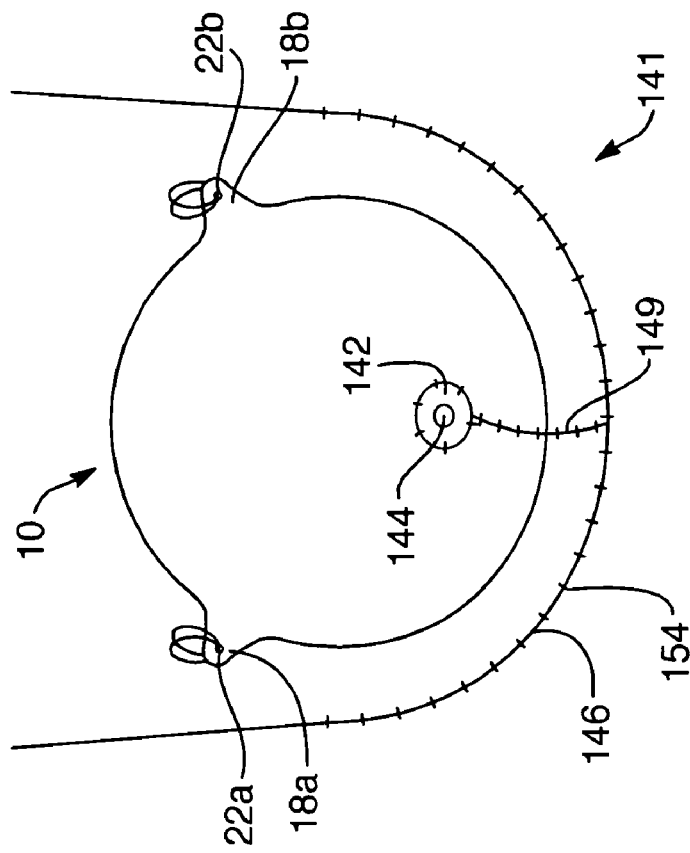
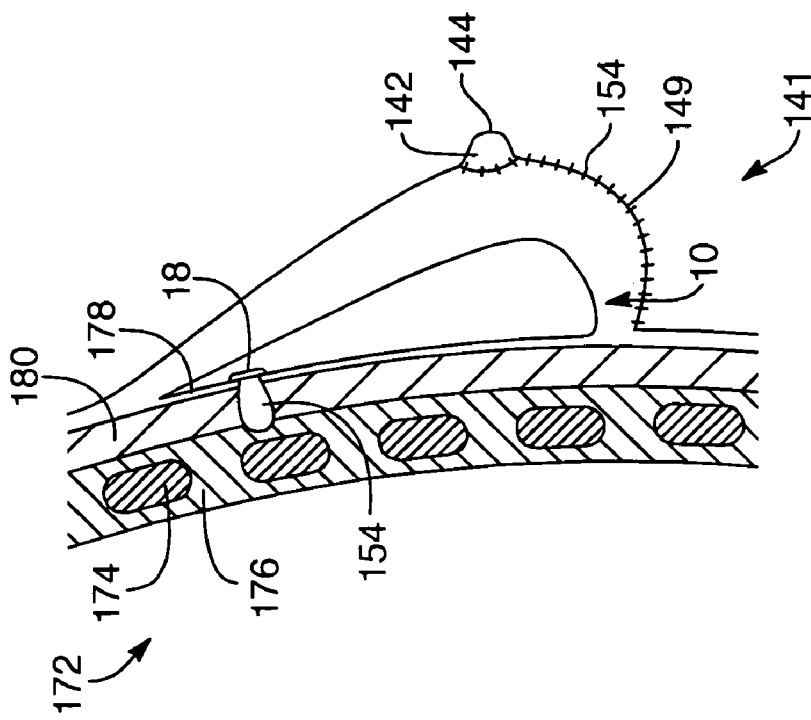
FIG. 21B
FIG. 21A

MASTOPEXY STABILIZATION APPARATUS AND METHOD

RELATED APPLICATIONS

This application claims priority to co-pending U.S. Provisional Patent Application Ser. No. 60/477,100 filed on Jun. 9, 2003.

BACKGROUND

1. The Field of the Invention

This invention relates to apparatus and methods for mastopexy or "breastlift" procedures and devices, and more particularly to devices and methods for increasing stability and longevity of mastopexy operations with augmentation.

2. The Background Art

Plastic and cosmetic surgery has existed for many years as a particular field of medicine, and surgery in particular. Reconstruction after accidents has been developed in order to replace, reconfigure, or otherwise ameliorate damaged tissues subjected to trauma through accident or other causes of disfigurement. In some circumstances, physiological difficulties arise due to damaged, broken, traumatized, or simply disproportionate members of the body. As the skill and experience of medical practitioners has increased, elective surgeries have become more common.

For example, cosmetically, breast enhancement surgeries have become more commonplace. Enhancement procedures may include augmentation of size and shape, as well as selective reduction.

One field of cosmetic surgery involves mastopexy or "breastlift" surgery. Factors such as pregnancy, nursing, physical activity, time, gravity, and the like may affect skin thickness and tone. As skin loses elasticity, shape and firmness consequently decline over time. Breastlift, or mastopexy, is a surgical procedure to raise and reshape breasts. However, no surgery can permanently delay the effects of gravity. Accordingly, mastopexy may alter size, shape, positioning, and volume of breasts. Bio-compatible implants may be inserted under muscle, or under mammary tissues above muscle in order to alter both firmness and size.

The causes of deformation for which mastopexy provides at least a partial remedy may include both stretching of skins and tissues, as well as a loss of elasticity of skins and tissues. Loss of elasticity is a result partly of age, and partly a result of the stretching processes. That is, all materials that are inherently elastic use up part of their elasticity in the process of stretching. Not all stretching is elastic; some is permanent with age, skin tissues are less elastic. Also, underlying tissues may thin, losing fulness and shape. Accordingly, these effects can continue.

Of particular concern is the continued effect of motion and gravity upon on mass subject thereto. Accordingly, continued stretching and drooping may occur after mastopexy. Moreover, in the situation of an augmentation procedure in conjunction with a mastopexy, an implant itself may add additional weight subjecting tissues to further invasion as gravity draws that mass downward. Thus, it would be an advance in the art to provide a method and apparatus to support an implant against the acceleration of gravity, in order to stabilize tissues after a mastopexy operation.

Moreover, complications may occur either unintentionally or simply as a matter of course. For example, any time the body is confronted with a foreign object, even though not chemically or biologically reactive therewith, the body tends to form scar tissue, and wall off the foreign object. Thus, scar tissue may form about an implant. Conventionally, the formation of a scar or a capsule has been relied upon to stabilize the position of an implant. However, implants may rupture, and scar tissue may rupture, altering the containing capsule. Also, the fibroblasts within scar tissue tend to contract. Nature shrinks scars from their initial size as the fibroblasts tend to organize and orient themselves like crystals, and then draw themselves shorter. However, such a contraction of scar tissue in an oblique shape results in closing up the area containing a volume. The result is a tendency toward spherical shape and higher pressures. Thus, texture, firmness, and shape may alter dramatically. What is needed is an apparatus and method for minimizing damage to body tissues, minimizing scarring, as well as an apparatus and method that do not rely on scar tissue formation to maintain dimensional stability temporarily during healing, nor permanently. Positioning is needed that does not wait for the many weeks required for scar tissue to form and stabilize.

Aesthetics may be effected by the reaction of bodily tissues to the presence of an implant. Likewise, alterations in the structure of an implant may also result in undesirable alterations in aesthetics. For example, capsular contracture (scar tissue shrinkage) may not only result in alteration of shape and firmness, but may actually result in rupture of an implant. Likewise, capsular contracture may result in selective shifting of position. Likewise, a rupture of scar tissue may result in shifting the location of an implant.

Thus, for example, what is needed is a system and method for temporary vertical load support in order to relieve the stress on tissues that must heal, in order to minimize scarring. Likewise needed is support for temporary sutures. That is, after surgery, suturing requires time to heal. Scar tissues will increase in width or area if loaded by weight or pressure. Likewise, stress of any wound or a suture location will cause considerable discomfort. Likewise, during scar tissue formation, weight or pressure against scarring tissue will cause additional discomfort.

Likewise, it may be advisable and useful to provide permanent support from weight in order to longer maintain the effects of a successful mastopexy procedure. Also, while many persons are involved in athletic pursuits as a means to recreation or improved health, vertical support against accelerations due to gravity or dynamic motions of an athlete would further enhance and maintain the effects of successful mastopexy.

Scarring responds to loading. If a scar in the skin is subjected to force, the scar will typically respond by localized damage that itself must heal by scarring. Accordingly, scars may be widened during healing by continued stretching or trauma. Moreover, many tissues in the body are comparatively soft. Accordingly, they are restrained by not only their own material properties and surrounding connective tissues but by the support from skin. Accordingly, a load on any particular part of soft tissue may be transferred, much as it would in a liquid, to exert a generalized omni-directional pressure. Thus, gravitational loads on an implant may result in a generalized omni-directional pressure against sutured tissues, causing additional stretching and exacerbation of scars.

It would be an advance in the art to provide vertical support against loading tissues directly as the force of gravity on scars and sutures. It would be an advance as well to provide support generally against the transfer of pressure into tissues in any direction.

As a capsule forms about a foreign body inserted into tissues, scarring forms around the periphery thereof. However, comparatively soft tissues may yield, tear, or otherwise permit migration of a prosthesis or implant. In the absence of other stabilization, and in the presence of unhealed scars, or even after scars have ostensibly formed interior to tissues to stabilize an implant, implants may migrate down or sideways. For example, lateral migration toward the arm, medial migration toward the sternum, downward migration toward the abdomen (inferior), as well as superior migration toward the collarbone, are all possible. In the presence of gravity, most common effects are typically lateral and inferior migration.

Thus, it would be an advance in the art to provide an apparatus and method for maintaining position laterally, medially, inferiorly, and superiorly against migration. Similarly, it would be an advance in the art to provide support against migration loads tending to shift locations of implants due to the stresses of the implant against other tissues during physical activity.

Many persons assume a symmetry to the human body that does not actually exist. Symmetry has been considered by those who study aesthetics to be a particularly pleasing effect. Nevertheless, the human body is not necessarily formed symmetrically. However, the lack of symmetry is still not desirable. Thus, in response to a mastopexy operation, symmetry may be sought as highly desirable. In fact, symmetry may be sought to a degree not originally present. Regardless, it would be an advance in the art to provide line symmetry to the degree possible as a result of mastopexy both along vertical (superior-inferior) lines and horizontal (lateral-medial) lines orthogonal thereto. Thus, positioning implants reliably with respect to one another is desirable, so they are each located along a lateral-medial direction at the same relative location relative to the remainder of the anatomy, positioned in a superior-inferior location equal with respect to one another, and properly located with respect to other anatomical features.

In yet another condition, certain implants are formed of a comparatively soft and resilient solid. Such implants tend to be formed of close-cell foamed polymers. Other implants contain gels. Yet other implants are formed of a shell or skin filled with a saline, glucose, or other solution that will be tolerated and disposed of by the body in the event of exposure to tissues.

The term "microbleed" describes migration of a liquid species through a solid. For example, a silicone liquid or gel may migrate through a wall, causing a reaction with tissues outside an implant. With the use of saline or glucose solutions, any microbleed of materials migrating through a wall of an implant may be absorbed and handled by the body through its normal processes. One result is the decrease of scarring in response to microbleeds of somewhat incompatible materials.

That is, for example, at a molecular or atomic level, chemicals migrate through other chemicals. Thus, an "impervious" material is really not so. Migration is simply very, very slow. Nevertheless, individual atoms, molecules, or the like may migrate through a comparative solid from one surface of a wall to the opposing surface of the wall.

As with all artificial procedures, precision can affect perceived quality of a result. Inasmuch as subsequent relaxation or drooping of tissue may occur after a mastopexy operation, surgeons may overcompensate in advance by "overlifting." Since the ultimate response of any specific body is a matter of some conjecture, problems may arise with overlifting not subsequently eliminated by additional stretching of tissues under the effects of gravity. Likewise, since tissues in the body are not necessarily identical or symmetrical, a certain degree of symmetry achieved during a lifting or mastopexy operation may be lost subsequently by disproportionate deflection (movement, stretching, etc.) after a mastopexy operation.

What is needed is a system and apparatus for providing mastopexy augmentation that provides a comparatively broad tolerance for a surgeon in the procedure involved, while resulting in a comparatively narrow tolerance or variation in the ultimate outcome. A procedure is needed that provides options for locating an implant, but subsequent, reliable stability.

Textures and dynamic reactions of implants vary. Some implants are formed of comparatively stable and lightweight foamed polymers, whereas others are formed of shells containing comparatively viscous liquids or gels. Yet others are comprised of shells of thin, flexible polymers filled with comparatively inviscid liquids such as saline and glucose.

Much of the driving force behind cosmetic surgery arises from personal valuations of aesthetics. One somewhat unnatural consequence of inviscid fill materials in implants is a dynamic ripple effect in response to motion or acceleration. Dynamic ripples may be visible on the surface of the skin. Dynamic ripples, sometimes called wrinkling, may occur due to the wave-like motion of subcutaneous liquids as filler within an implant.

Soft tissues tend to have a more solidus nature, although soft, and easily deflected. Nevertheless, connective tissues have a certain elasticity present therein providing a certain texture and stability. By contrast, inviscid liquids may result in surface rippling, particular if the implant is only subglandular rather than sub-muscular.

Thus, what is needed is an improved apparatus and method providing a simple, reliable, aesthetically appealing mastopexy with augmentation. Reduced side effects, including internal scarring about the capsule surrounding an implant, as well as reduced scarring, stretching, and the like of sutures in the exposed skin would be desirable. Temporary and permanent support of implants, in order to relieve tissues from the forces of gravity in combination with the weight of implants, would be an advance in the art. Stabilization in order to reduce scarring, stiffness, capsular contraction, and scarring in reaction thereto would be an advance in the art.

It would be an advance in the art to reduce microbleed diffusion of filler material by reducing forces or pressures driving such diffusion. Reducing effects of such diffusion should include reducing weight, stress, pressure, and the like tending to strain, stress, damage, or irritate tissues surrounding an implant. It would be an advance in the art to provide increased resistence to inviscid implant fillers by stabilizing the outer shell more substantially, while eliminating or reducing substantially the need for overlifting. Reducing the reliance on scarring as a containment mechanism for the capsule surrounding an implant would likewise advance the art.

BRIEF SUMMARY AND OBJECTS OF THE INVENTION

In accordance with the foregoing, a method and apparatus for stabilizing mastopexy operations may include providing a containment vessel, serving as an implant, comprised of a container, bag, molded shell, or the like for holding a filling material. The back plane or back surface of the implant may conform to the chest wall below (within) or above (without) the pectoral muscles. The implant may have anchor tabs, sutures, tethers, or the like for suturing or otherwise anchoring the implant against the chest wall, against muscles, or the like in order to stabilize the location and support the weight thereof. Sutures or other anchors may serve during scarring and temporary duration of the healing process, as well as permanently.

Such an apparatus and method may reduce complications including contracture (contraction) of capsular scars, may reduce scar formation, may reduce the risk of deflation or rupture of implants as well as reducing rupture of scars formed in the capsular region. Moreover, an apparatus and method in accordance with the invention may reduce excessive firmness and stabilize both the aesthetic and dynamic shape of an implant.

In certain embodiments, an apparatus and method in accordance with the invention may reduce thickening, firmness, and contraction of the layer of tissues surrounding an implant and forming a capsule therearound. In certain embodiments, a shell may be formed of a polymeric material, a reinforced polymer, an expanded polymer, or the like, and may contain a liquid, gel, solid, or foam. In one presently contemplated embodiment, a silicone compound, such as dimethylsiloxane composition may form a shell, and may have embedded therein certain fibrous materials, such as Kevlar®, nylon, rayon, dacron, suturing materials, combination thereof, or the like to provide additional tensile strength and stability thereto. In certain embodiments, an implant or device in accordance with the invention may include tabs extending from the back plate thereof or back wall thereof for receiving a suture. Alternatively, sutures themselves may actually be embedded in the back plate (e.g. back surface or wall) of a device in accordance with the invention in order to simplify surgical procedures.

In certain embodiments, tabs may be co-located with or formed as extensions of the back surface of an implant device. Tabs may be located at the ten o'clock and two o'clock positions relative thereto. The 10:30 and 1:30 positions have certain stress support advantages. In an alternative embodiment, additional tabs may be located at other locations, such as, for example, a five o'clock and seven o'clock position, a four o'clock and eight o'clock position, or at a single six o'clock.

In an apparatus and method in accordance with the invention, sutures may use a variety of needle types, including a taper point for soft tissue, or a cutting point for piercing the chest wall in order to anchor to the rib cage. Sutures provided with a device in accordance with the invention may include a needle secured thereto and packaged therewith. Accordingly, a device may include a shell having a filling material placed in the shell during the manufacture thereof, or added subsequently by a surgeon.

In certain embodiments, reinforcing materials may include suture material embedded in at least the back plate or back wall of a device to provide tension support. In certain embodiments, multiple layers, and loops of suture material may be embedded in the back surface or back wall of an implant device in order to provide various locations for suturing. In certain embodiments, a suture may be embedded or introduced independently to secure a tab to muscle, ribs, cartilage, or the like.

A needle may arrive connected to suture material embedded in a back wall of an implant device. Needles may be provided with a protective covering, about themselves or including the suture material rolled up, in the form of a removable or breakable protection, such as a ring, loop, spool, cap, envelope, clip, or the like.

A method and apparatus in accordance with the invention may provide stabilization of the anatomical position of an implant associated with a mastopexy operation in order to reduce gravitational load on remaining tissue, scars, sutures, and the like. Accordingly, such a method and apparatus may reduce difficulties and negative results associated with the aesthetic appearance of the mastopexy result. They may reduce difficulties with improper positioning, lateral or medial displacement, inferior or superior displacement, unnatural shape, asymmetry as to superior-inferior positioning or relative positioning between pairs of implants, as well as lateral-medial symmetry between pairs of implants. Likewise, they may reduce rippling, wrinkling, and the like sometimes associated with the dynamic response of inviscid filling materials within a shell of an implant.

In an apparatus and method in accordance with the invention, temporary, permanent, or both types of support may be provided for an implanted device. Temporary support may be provided for reduction of scarring, migration, dislocation, and the like during healing. Permanent sutures may support implants during subsequent vigorous activities, athletics, and the like to improve the longevity or duration for which the mastopexy operation may be effective.

BRIEF DESCRIPTION OF THE DRAWINGS

The foregoing and other objects and features of the present invention will become more fully apparent from the following description and appended claims, taken in conjunction with the accompanying drawings. Understanding that these drawings depict only typical embodiments of the invention and are, therefore, not to be considered limiting of its scope, the invention will be described with additional specificity and detail through use of the accompanying drawings in which:

FIG. 8A is a schematic front elevation view an alternative embodiment of an apparatus in accordance with the invention having diagonally-laid reinforcing fibers, which may be used with the homogeneously molded tabs, otherwise attached tabs, or the embedded suture material as illustrated in FIGS. 1–7;

FIG. 8B is a schematic front elevation view an alternative embodiment of an apparatus in accordance with the invention having diagonally-laid reinforcing fibers, which may be used with the homogeneously molded tabs, otherwise attached tabs, or the embedded suture material as illustrated in FIGS. 1–7, and including in this embodiment additional inferiorly located stabilization tabs, which may also be used in conjunction with, separately from, or absent in favor of, inferiorly located suture lines;

FIG. 9A is an exploded, side elevation, cross-sectional view of one embodiment of a laminated back plate for a device in accordance with the invention;

FIG. 9B is a side elevation, cross-sectional view of a back plate in accordance with the invention, formed either by lamination of the layers of FIG. 9A, or by infusion molding of a resin into a reinforcing gauze or fiber reinforcing material;

FIG. 21A is a schematic, side elevation, cross-sectional view of an augmented mastopexy illustrating anchoring of an implant in accordance with the invention;

FIG. 21B is a schematic front elevation view of the illustration of Figure . . . the anatomy and implant of FIG. 21a;

DETAILED DESCRIPTION OF THE PREFERRED EMBODIMENTS

It will be readily understood that the components of the present invention, as generally described and illustrated in the Figures herein, could be arranged and designed in a wide variety of different configurations. Thus, the following more detailed description of the embodiments of the system and method of the present invention, as represented in FIGS. 1 through 27 is not intended to limit the scope of the invention, as claimed, but is merely representative of the presently preferred embodiments of the invention. The presently preferred embodiments of the invention will be best understood by reference to the drawings, wherein like parts are designated by like numerals throughout.

Figure 1:
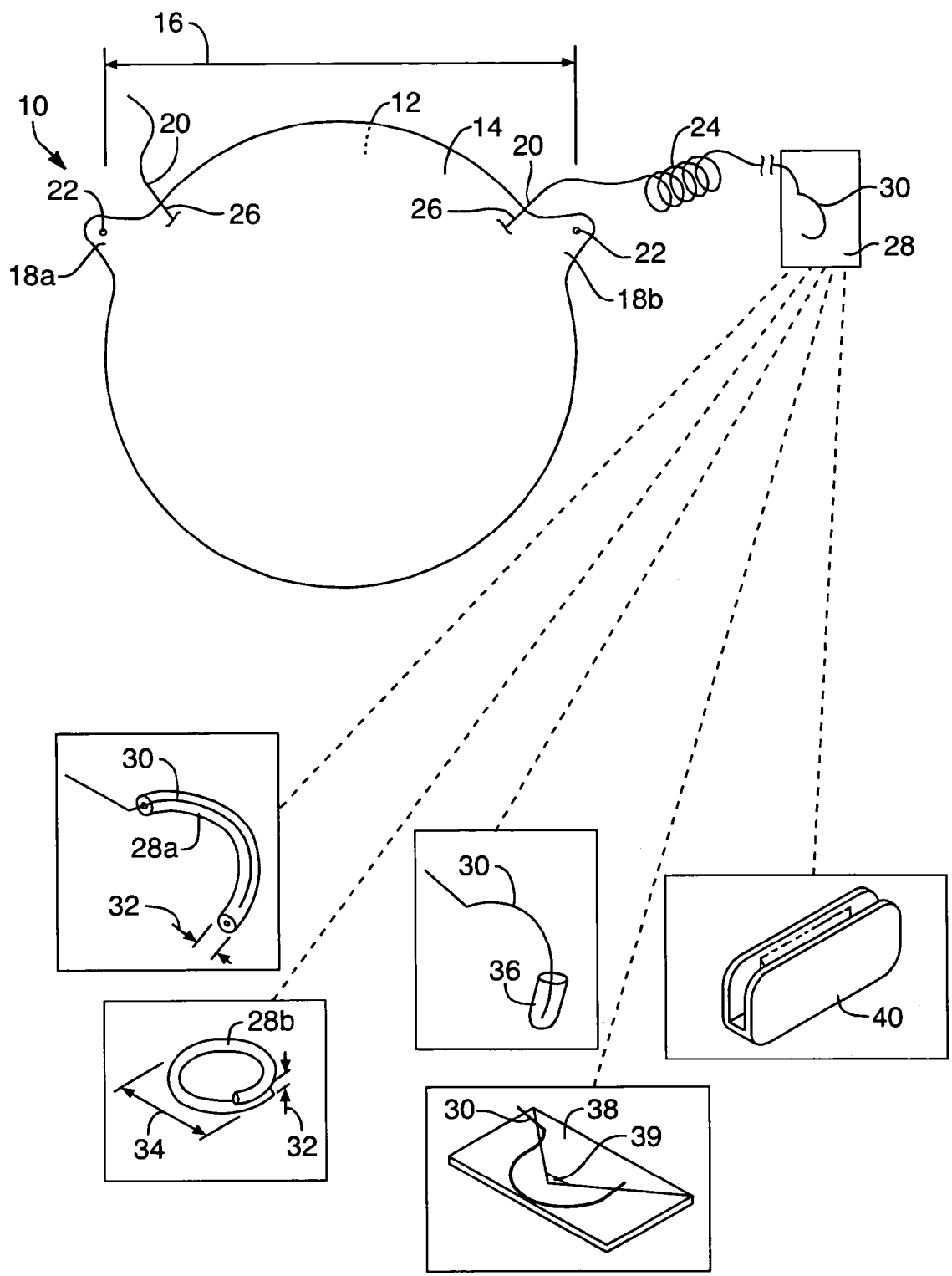
FIG. 1 is a schematic diagram of an apparatus in accordance with the invention illustrating optional embedded sutures, integrated tabs, and protection for needle associated with a suture material.

Referring to FIG. 1, an apparatus 10 or implant 10 may be formed to include a back plate 12 and a pocket 14 of a flexible, elastically deformable material. The pocket 14 and back plate 12 may be formed as a single homogeneously molded container. The back plate 12 may typically be formed to appear flat, and the pocket 14 may be rounded, hemispherical, or anatomically shaped. In some presently contemplated embodiments, the pocket 14 represents a portion of substantially a hemisphere and the back plate 12 represents a substantially flat base thereto.

The back plate 12 and thus the overall apparatus 10 may be formed to have an outside diameter 16 and a corresponding wall thickness thereof. The material of the implant 10 or apparatus 10 may be transparent, translucent, or opaque. In certain presently contemplated embodiments, the material may be substantially transparent, wherein the shell may actually tend to scatter light diffusing the image of light therethrough somewhat.

In one embodiment, tabs 18 may be homogeneously formed with the back plate 12 to project therefrom for securing the apparatus 10 to the anatomy of a user. As an alternative, as an adjunct, or as a combination with the tab 18, a suture 20 may be embedded to extend from the back plate 12. An aperture 22 in the tab 18 may be formed explicitly during manufacture. Alternatively, an aperture 22 may simply be formed by perforation during the process of suturing to the tab 18. Trailing letters on reference numerals herein indicate specific instances of the generalized item identified by the leading reference numeral.

In certain embodiments, a tab 18 may be formed to use in conjunction with a previously embedded suture 20. In yet another embodiment, the suture 20 may be embedded to extend from the back plate, having a length 24 or extra length 24 of suture material for completing a suture. Likewise, an anchor portion 26 of the suture line 20 may extend radially into the back plate 12 a distance, or even completely across the diameter 16 of the back plate 12. Thus, the suture 20 may provide substantial support of the back plate 12 and apparatus 10.

At a distal end of the suture line 20, a protective sleeve 28 may enclose a surgical needle 30 secured thereto. A surgical needle 30 may be threaded by a surgeon with surgical suture line 20, or may come premanufactured or preconnected to the suture line 20. The extra length 24 may be enclosed with the needle 30 in the sleeve 28.

In certain embodiments, various protective sleeves 28 may be used. For example, a tubular protection device 28a or tube 28a may enclose a portion or all of a needle 30. At a minimum, any cutting surface or point of the needle 30 is best protected in order to protect both a patient and the device 10 from puncture.

In an alternative embodiment, a coil 28b of tubular material may extend circumferentially through 180 or even 360 or 720 degrees. Accordingly, the ring 28b forms a protective sheath, round in shape to prevent snagging prior to deployment of the needle, and if sufficiently elastic and sufficiently rigid or stiff, may provide the ability to clip a roll of extra suture material 24 therebetween. A diameter 32 of a tubular material may be oversized to receive a needle easily, relying on the curvature of the needle to distort and secure the tube 28 thereto. Alternatively, the coil 28b may be formed of a diameter 34 compatible with the arc of a needle 30, and have a diameter 32 selected to properly receive the cross section of a needle 30.

In one embodiment, a simple cap 36 may be formed to protect a needle point. Various materials, including rubber, latex, other elastomeric polymers, hard plastics, waxes, cork, expended polymer foams, and the like may be used to form the cap 36. In one embodiment, the cap 36 may be formed to break. In other embodiments, the cap 36 may be comprised of a hard outer shell to resist penetration by the needle 30, with an inner material formed of a softer material such as wax, plastic, foamed plastic, rubber, elastomeric material, or the like for securing the needle 30 until ready for use.

In yet another alternative embodiment, a clip 40 may receive a needle snapped thereinto. The clip 40 may have rounded edges and a circular, rectangular or other polygonal shape. The clip 40 may be formed to provide little or no resistance to motion across a tissue surface, when secured to the device 10, in order to minimize interference prior to deployment of the needle 30.

In yet another alternative embodiment, a simple plastic, paper, fabric, or other type of envelope 38 may be formed to receive and hold a needle and suture materials. A flap 39 may be removably secured to hold the suture 20 and needle 30 in place until deployed. After location of the apparatus 10 or implant 10, the envelope 38 may open to provide the needle 30 and suture 20 for anchoring the apparatus 10.

Figure 2:
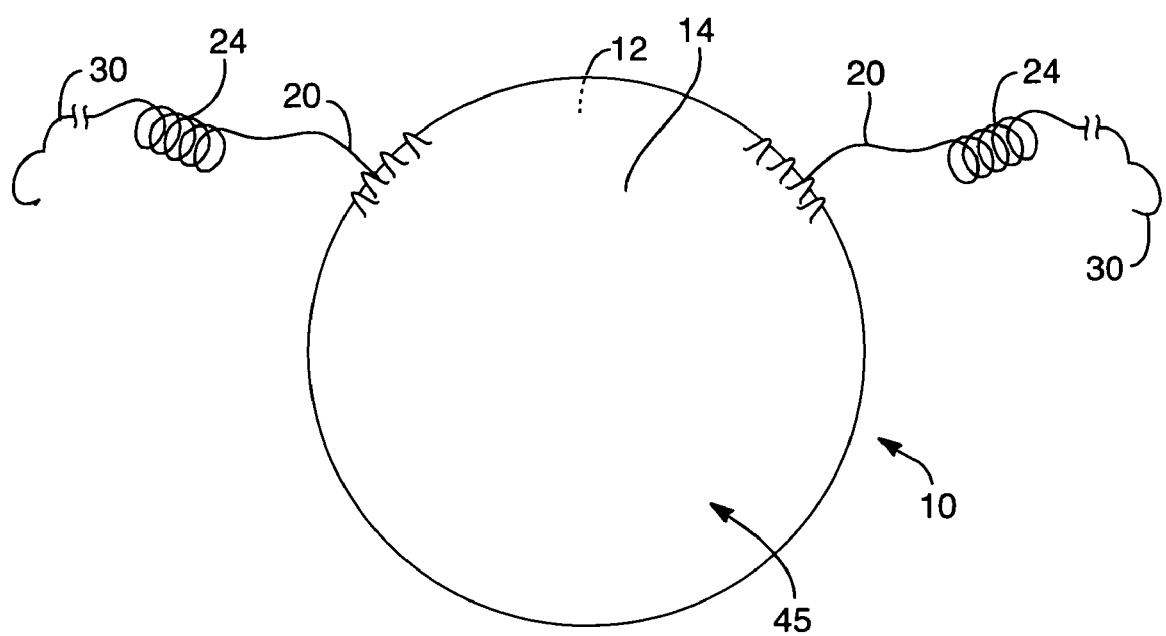
FIG. 2 is a schematic of a front elevation view of one embodiment of an apparatus in accordance with the invention providing suturing loops extending from or near an edge of a back wall of an apparatus to receive sutures therethrough for anchoring using the suture material (line) and needle presented by the apparatus.

Referring to FIG. 2, in certain embodiments, additional loops 43 or embedded materials such as reinforcing strands 43 or embedded suture materials 43 may extend radially from the periphery of the back plate 12 to provide anchor points for connecting the suture 20. In certain embodiments, the needle 30 and suture material 20 or line 20 may simply pierce a tab 18. Alternatively, reinforcing strands 43 or embedded loops 43 may extend from the periphery of the back plate 12 to receive one loop or multiple loops of the suture 20.

The pocket 14 and back plate 12, are typically very flexible. In some embodiments, the pocket 14 and back plate 12 may be formed seamlessly by a method such as rotational molding in order to eliminate seams, edges, mold flashing, and the like. Meanwhile, filler may occur either during the manufacturing process, or subsequent thereto. During installation (e.g. insertion and anchoring), or even just before or after insertion of the apparatus 10, the pocket 14 may be filled with a suitable material.

Typical filler materials 45 may include soy oil, saline solution, silicone gel, hydro gel, polyvinylprolidone (PVP), polyethylene glycol (PEG), hyaluronic acid, or the like. Materials may be chosen for their density, viscosity, and biocompatibility, as well as the ability to either resist microbleeding (e.g. weeping, microscopic level transmission through walls), and the like. Likewise, materials may be selected in order to optimize the ability of the body to deal with them in trace amounts in the instance of a microbleed.

Fill materials may be selected in accordance with various features including shell compatibility, the antimicrobial nature thereof, and the stability over time. Stability may include various properties including dimensional stability, texture, chemistry, and the like. Similarly, materials may be selected for their nonimmunogenic and nonallergenic properties. Most materials should be screened to assure that they are noncarcinogenic, nontoxic, and otherwise completely compatible biologically. This may be significant in the event of microbleeding through the walls of the back plate 12 and pocket 14, or in the event of a rupture or leakage into the body tissues.

Radiolucence is a useful property in assuring that radiological evaluations still operate properly. For example, a mammogram in the presence of radiopaque materials can cause problems with the proper operation of x-ray systems.

A material that is absorbable by the body may protect against dangerous consequences in the possible event of rupture of a shell. Rupture of the shell might release materials into tissues of the body. An ability to absorb or metabolize a filler material 45 may be a high priority feature in order that escaped materials be carried away by the body waste disposal functions rather than remaining to migrate to various places where they may cause eventual difficulties.

Maintaining pH-neutral conditions, and osmotically neutral conditions will also assist in the event of possible leakage or rupture. The ability to maintain a material wrinkle-free or ripple-free is typically a function of viscosity and the construction of the apparatus 10. The palpability of material may affect the choice since solidus materials may be detectable, but inviscid materials may be detectable somewhat as being less viscid than natural materials. Similarly, materials that have suitable cost, rather than being exotic and expensive, as well as materials that will minimize the effect of capsular contracture are also to be sought. Capsular contracture is usually instigated by microbleeding of small amounts of materials that cause reaction by the body.

Figures 3A, 4A:
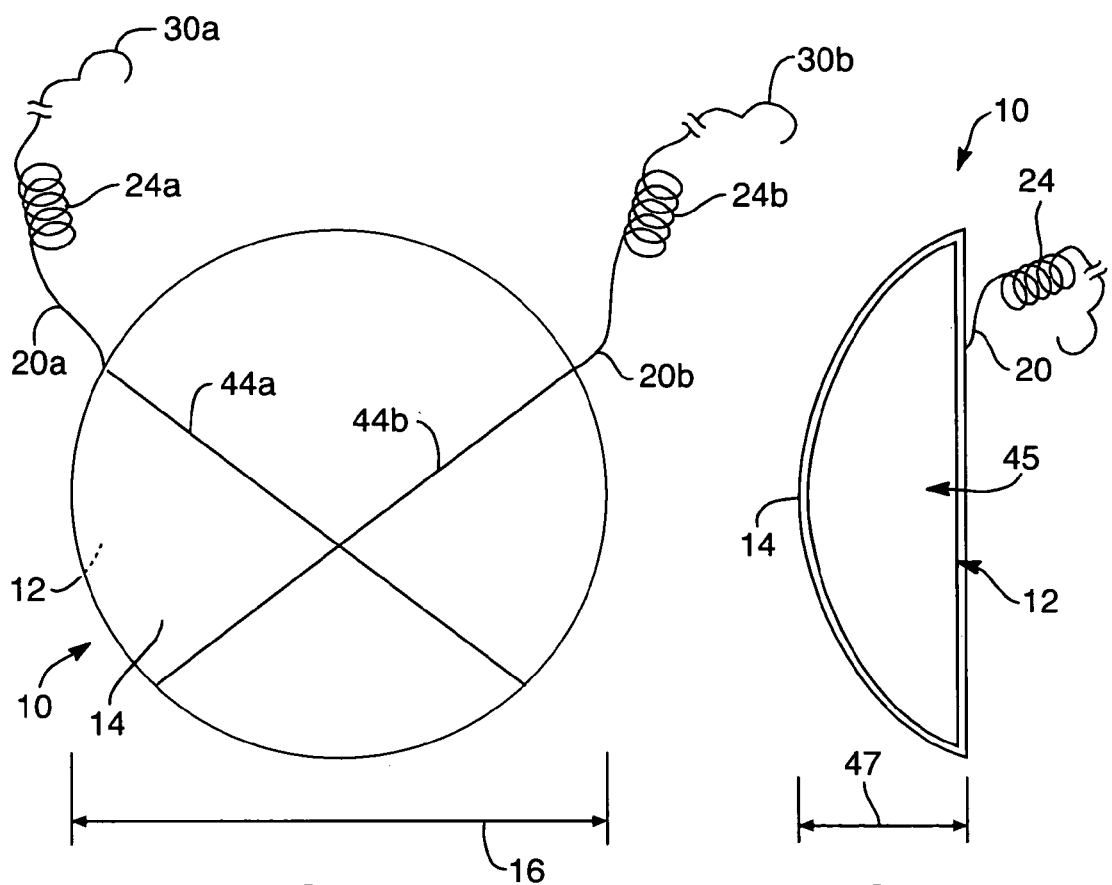
FIG. 3A is a schematic, front elevation view one embodiment of an apparatus in accordance with the invention relying entirely on sutures presented by the apparatus.
FIG. 4A is a schematic side elevation view of one embodiment of an apparatus in accordance with the invention provided with alternatives of a presented suture and a tab for receiving a suture, which may be used in combination, or independently from one another as alternative embodiments.
Figures 3B, 4B:
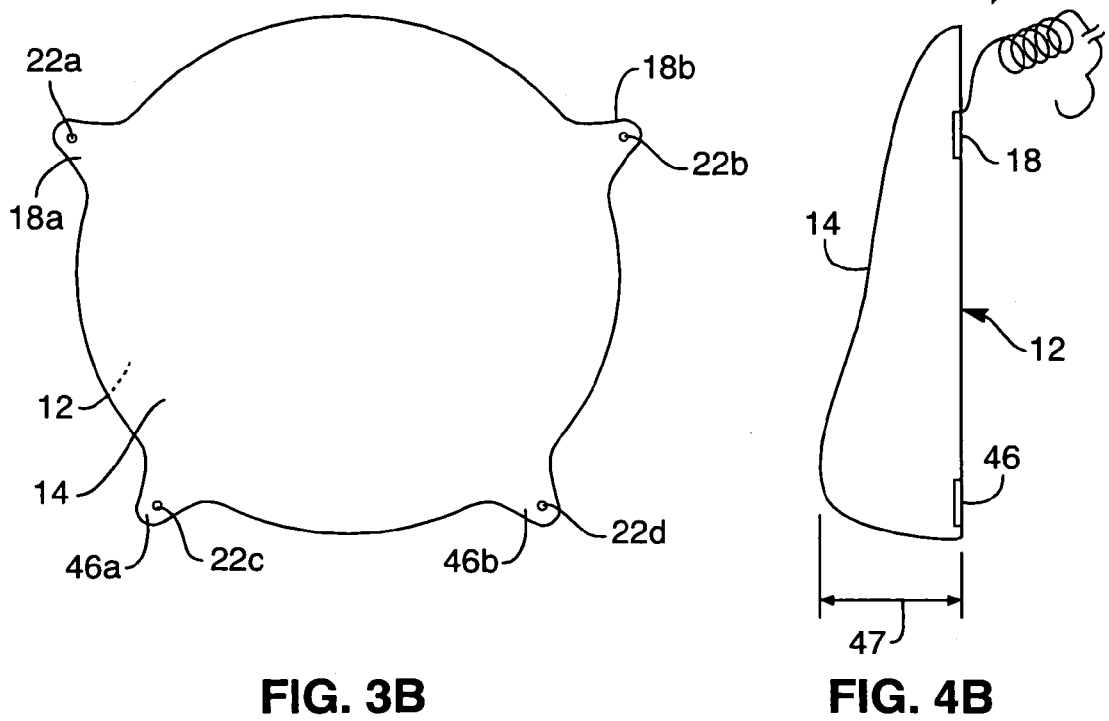
FIG. 3B is a schematic front elevation view of one alternative embodiment of an apparatus in accordance with the invention relying on tabs for receiving a suture therethrough.
FIG. 4B is a schematic side elevation view of one embodiment of an apparatus in accordance with the invention providing an anatomically shaped implant showing alternative embodiments of tabs, suture and needle, which may be used individually, exclusively, or in combination.

Referring to FIG. 3A and FIG. 3B, the suture 20 may be embedded within the back plate 12 in a direction devised to optimize support by the suture 20 and the access thereto. In one embodiment, the embedded strands 44 of the suture 20 may extend across the back plate 12 a distance select to provide adequate transfer of load from the suture 20 into the back plate 12. Multiple suture lines 20 may be embedded by way of individual strands of a braided suture. Alternatively, a single braided suture 20, or band may extend from the periphery of the back plate 12 for anchoring to the tissue of a chest wall or of chest muscle (e.g. pectoralis major).

Referring to FIG. 3B, an alternative embodiment may rely on no embedded sutures 20 presented, and instead rely only on tabs 22. In the illustrated embodiment, superior tabs 18a, 18b may also be augmented by inferior tabs 46a, 46b. As a practical matter, relatively minor loads exist to require the use of the tabs 46. By the same token, more athletic persons may desire, or it may be advantageous to provide, the tabs 46 to protect against dynamic loads. That is, the tabs 18a, 18b normally protect against gravitational loads (weight) of the apparatus 10 acting against tissues therebelow. However, in dynamic activities such as running, and the like, the inferior tabs 46a, 46b may provide dynamic stabilization against superior, lateral-medial, or transverse movement (toward and away from the chest wall).

Referring to FIG. 4A, in one presently contemplated embodiment, the apparatus 10 may be substantially formed as a more-or-less flat back wall 12, back plane 12, or back plate 12, and a hemispherical pocket 14. The projection 47 or depth 47 of the pocket 14 may be selected according to the manufacture of the pocket 14 or the amount of the fill material 45 enclosed therein. A surgeon at or shortly before the time insertion of an apparatus 10 may alter or introduce the filler 45. In the illustrated embodiment, a suture 20 is shown, but the apparatus of FIG. 4A may also be used with any of the configurations illustrated in FIGS. 1–3B.

Referring to FIG. 4B, an alternative embodiment of an apparatus 10 may include a "anatomically formed" pocket 14. This embodiment, a preferential projection 47 may favor the inferior portion of the pocket 14. The pocket may be shaped to produce this effect. Nevertheless, in the apparatus 10 in accordance with the invention, it has been found that no additional anatomic drop or preferential location of the maximum projection 47 is required to produce the desired and adequate augmentation effect.

Figure 5:
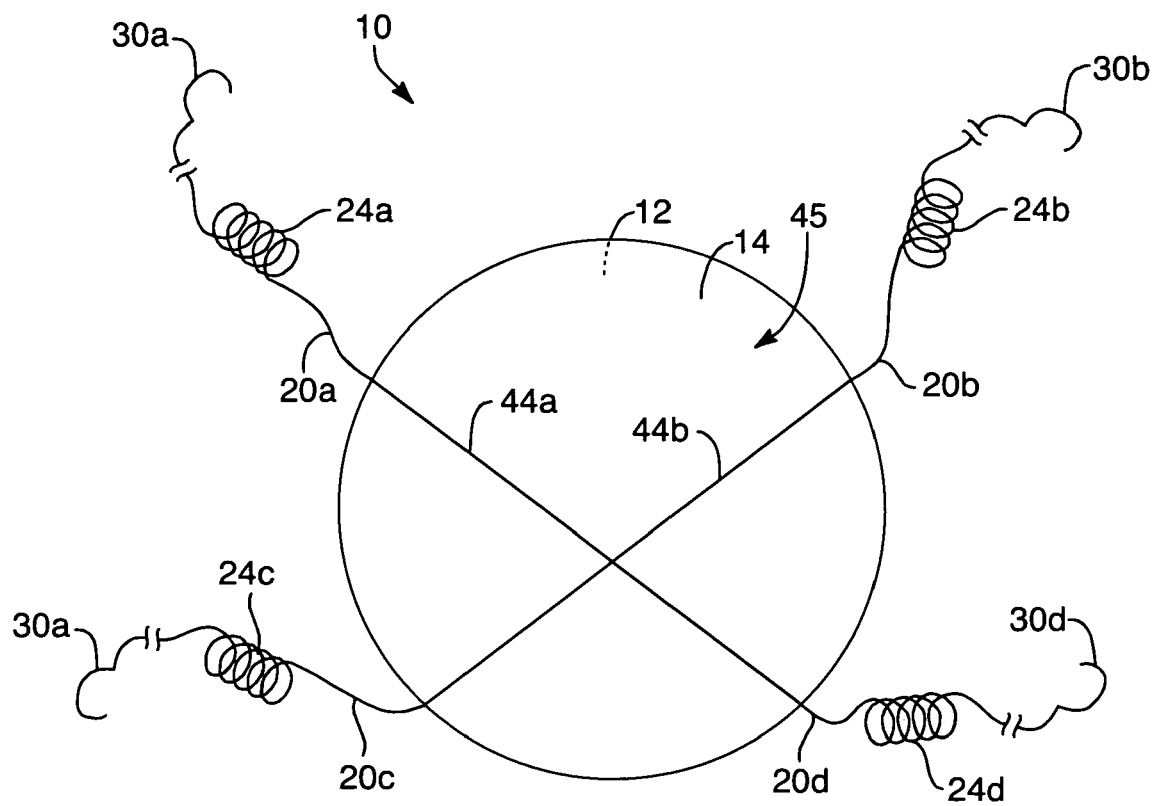
FIG. 5 is a schematic front elevation view of an apparatus in accordance with the invention including multiple sutures along both the superior edges and inferior edges of the apparatus, and may be used in combination with the tabs of FIG. 3B, and the additional reinforcing loops of FIG. 2.

Referring to FIG. 5, the apparatus 10 may include multiple sutures 20 embedded in the back plate 12. In certain embodiments, the locations of the extensions or presentation of sutures 20a, 20b may approximate the ten o'clock and two o'clock positions. Similarly, the presentation of the sutures 20c, 20d may approximate the five o'clock and seven o'clock positions. Thus, the sutures 44a, 44b embedded in the back plate 12 may not necessarily cross in the center of the apparatus 14. In alternative embodiments, a more symmetric support system may be formed. That is, the locations of the crossing of the embedded sutures 44a, 44b may be centered or placed in any other suitable location in order to provide both a supporting force therefrom, and a proper location of the sutures 20 for use. One good spacing places sutures 20 at ninety degrees from one another.

Figure 6:
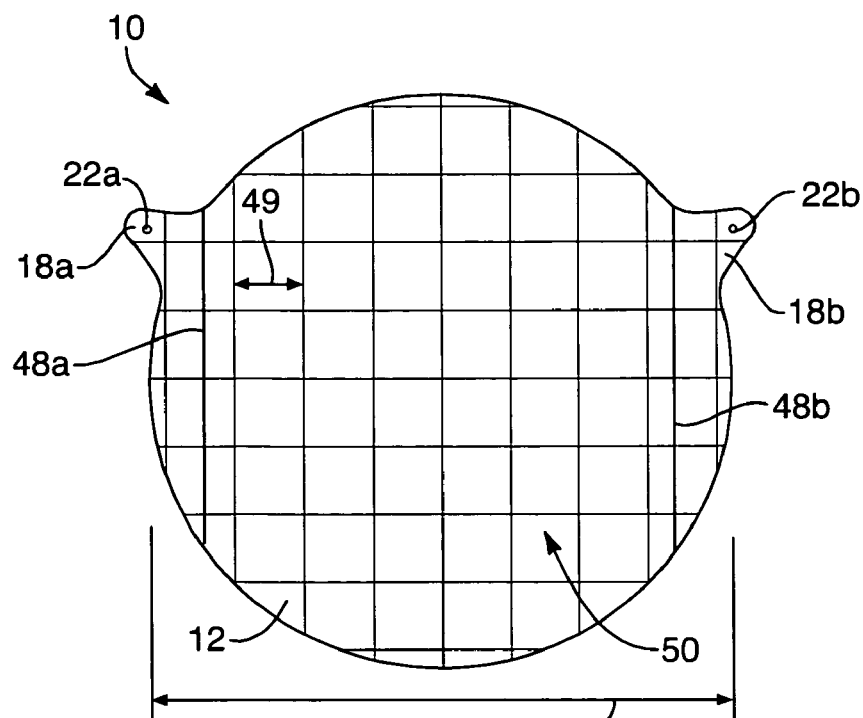
FIG. 6 is a schematic front elevation view of one alternative embodiment in which homogeneously molded tabs extend from a back plate of the apparatus, including a reinforcing material extending therethroughout to transfer loads effectively.

Referring to FIG. 6, one embodiment of a reinforced composite material in a backplate 12 may include a reinforced fiber composed of either single parallel strands, randomly oriented strands, or a mesh fabric having a selected interstitial distance 49 therebetween. As a practical matter, reinforcing fibers 48 may be oriented in substantially horizontal and vertical directions in order to provide multidirectional stress support. In the embodiment of FIG. 6, the tabs 18 provide locations for anchoring the apparatus 10 to the body.

Figure 7:
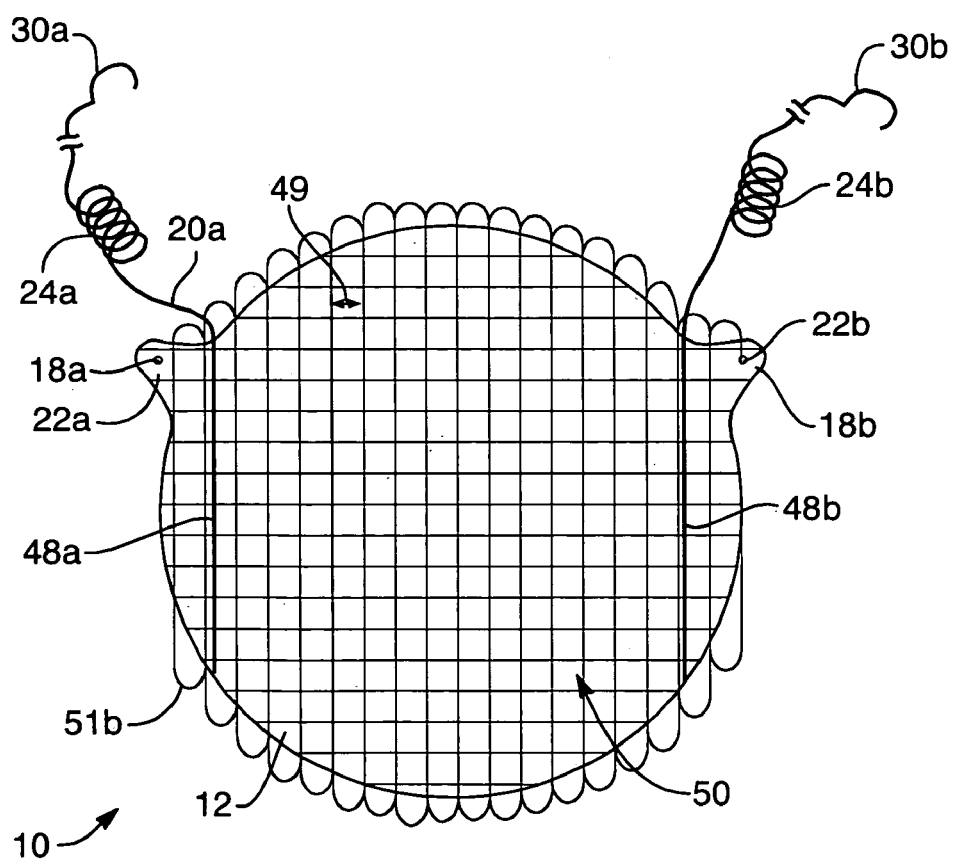
FIG. 7 is a schematic front elevation view of a device in accordance with the invention illustrating optional reinforcing material embedded in the back plate of a transparent or translucent implant device, and having suture materials embedded therein, as well as homogeneously molded tabs extending at the periphery of the device for receiving sutures, although the embedded suture and the integrally molded or homogeneously molded tab may be used exclusive of one another, or in combination with one another, and thus may be regarded as representing both alternative embodiments without each other, and the optional embodiment in which both are present.

Referring to FIG. 7, a similarly arranged pattern of reinforcing fibers 48 may be embedded within a backplate 12 of an implant 10 or apparatus 10 to be supported by a suture 20. Sutures 20 may be arranged at suitable locations about the periphery of the backplate 12 in order to provide both support, orientation, and stabilization in a lateral-medial direction, as well as support in a superior-inferior direction.

In certain embodiments, either the reinforcing fibers 48, or other fibers specifically included for the purpose, may extend out from the edges of the backplate 12 to form loops 51a at the superior edge of the backplate 12, or as loops 51b at the inferior edge of the backplate 12. That is, for example, the suture 20 may be connected at multiple locations about the edges of the backplate 12 in order to reduce the localized stress.

For example, the tab 18 may be relied upon for receiving multiple loops of a suture 20. Nevertheless, an array of loops 51 distributed about a region or the entire periphery of the backplate 12 may receive the suture 20, thus distributing the overall loading, and providing additional support and stability.

Nevertheless, loops 51 need not be contiguous or integrated with the reinforcing fibers 48 forming the overall mesh 50. The loops 51 may be formed of the suture material, a netting, or other looped, lacey, or otherwise perforated array of strands. In yet another alternative embodiment, the loops 51 may be absent and the suture 20 may simply be formed of a type of suture material suitable for supporting the entire load on a single strand. Thus, the suture 20 may actually be embedded as the only or one of many reinforcing strands 48.

In certain embodiments, the variation in suture materials 20 may be substantial. Suture materials may range from those that biodegrade relatively quickly, to those that remain substantially permanently. For example, certain suture materials are monofilament synthetics. To the lay person, these appear like fishing line. Suture materials may also be braided. Sizes and strengths may vary by almost an order of magnitude. Accordingly, the suture 20 may be formed of reinforced, braided, or substantially larger gauges of material in order to improve its single-strand strength.

Suture materials 20 may include a variety of coated or uncoated sutures 20. For example, sutures may be braided and uncoated, in order to provide better purchase against tissues. Nevertheless, some individuals may consider the apertures or interstices within braided sutures to harbor bacteria or the like. Accordingly, some sutures may be braided and coated in order to provide them more of a monofilament behavior or characteristic. Typically, monofilament sutures are formed as a drawn single fiber of a single synthetic material. Synthetic materials often have a stiffness and coefficiency of elasticity that inhibit the ability to form a knot well. Likewise, the particular stiffness of synthetic monofilament materials may be substantially greater than that of graded multi-filament materials.

Nevertheless, monofilament suture materials typically provide low tissue reactivity. The smooth surface does not permit incursion of bacteria. Likewise, natural materials may actually be somewhat monofilament in nature, but are typically bioreactive, immunoreactive, or the like.

Some materials considered for use as the suture 20 may include vicryl that represents a material named polyglactin 910. Such material maintains a high proportion of initial strength (e.g. seventy percent at ten days and thirty percent at twenty days). It can be biodegraded, absorbed, or otherwise disposed of by the body within sixty to ninety days.

An alternative material is a coated vicryl that contains a mixture of calcium stearate and polyglactin 370 and maintains one hundred percent strength for approximately forty-five days before decreasing to seventy percent at fifty days. Another material is polydioxalone, also called PDS. This material retains seventy percent strength for approximately twenty-one days before reducing to about fifty percent strength in thirty-five days. This material is typically absorbed by the body within one hundred eighty days and results in minimal tissue reaction.

Catgut, for all the visions it conjures up, is actually a thinly refined strip of intestinal tissues from sheep, such as the submucosa of sheep, and may be taken from the intestinal serosa of cattle. This material maintains tensile strength for only approximately ten days before being degraded. Chromatised catgut may retain tensile strength for twenty to forty days, and all forms of catgut may result in a moderate degree of tissue reaction.

In addition, other materials may include nylon, a non-absorbable synthetic monofilament suture material. Ethibond is a braided, non-absorbable synthetic suture material formed of polyester fiber under a coating a polybutilate for lubrication, and having advanced tensile strength properties.

Natural silk is actually a protein fiber used for suture for millennia. Stainless steel may be used since it is inert, has virtually no tissue reaction, and can last permanently. Nevertheless, steel often presents some difficulty with knotting, since it has considerable stiffness. Nevertheless, a single strand of properly formed stainless steel may serve as a suture 20, and adequately support the entire weight of the apparatus 10.

Referring to FIG. 8, the mesh 50 may be oriented at a diagonal with respect to the principal axes of the device 10 or the human body. Since the use of multiple tabs 18 or multiple sutures 20 on opposite sides (lateral vs. medial) of the apparatus 10 will provide largely vertical (superior-inferior axis) support, the horizontal or lateral support (e.g. lateral-medial axis) will still be required. Expecting overlying tissues to provide this inherently may not be an accurate model. Accordingly, by spacing apart the tabs 18 or the sutures 20, stress may be distributed in both horizontal and vertical (nominal) directions. Accordingly, providing a bias orientation to the mesh 50 may more readily distribute stresses within the back plate 12 of the apparatus 10. The angles between the various fibers 48 may be right angles, or may be arranged at any other suitable angle.

Referring to FIG. 8B, an apparatus 10 in accordance with FIG. 8A may be anchored with inferior anchors 46a, 46b, as well as the superior anchors 18a, 18b. As a practical matter, all anchors 18, 46 may be referred to as anchors 18. As a matter of clarity, one may think of the anchors 46 as inferiorly oriented compared to anchors 18.

Referring to FIG. 9A, a mesh 50 may be laminated between layers 52, 54 of a backplate 12 material. For example, one may consider the cover 52 facing anteriorly on the backplate 12, with the base 54 facing posteriorly. A suitable bonding agent, including glues, polymers, solvents, or the like may be used for bonding the mesh 50 to the cover 52 and base 54. Alternatively, heat, ultrasonic waves, or another material may be used to embed one or both of the cover 52 and base 54 to the mesh 50. Similarly, the layers 52, 54 may actually extend beyond the edge of the mesh 50, in order to seal the mesh 50 away from tissues, and the body. Alternatively, the backplate 12 may be formed with the mesh 50 extending from the cover 52 and base 54, in order to provide attachment access for sutures 20.

Referring to FIG. 9B, one embodiment of an apparatus 10 may include a matrix 56 of polymeric material cast around and through a mesh 50. Accordingly, an insert formed of the mesh 50 may be placed in a mold, and the resins melted or otherwise flowed to form the embedded matrix 56 of polymeric shell material. Again, the mesh 50 may extend through part of a tab 18, 46 or throughout the entire backplate 18. Alternatively, the mesh 50 may be formed as only a structural element extending through any selected portion of the backplate 12 or the remainder of the pocket 14 of the apparatus 10. For example, in one embodiment, the mesh 50 may actually be formed into the entire wall of the apparatus 10. Nevertheless, matters of structural integrity, as well as manufacturing simplicity and cost may direct the decision as to the mesh size 49, the extent of the mesh 50, the material thereon, the orientation of the angle between the mesh fibers 48, the enclosure or exposure of the mesh 50, and the like.

Figure 10:
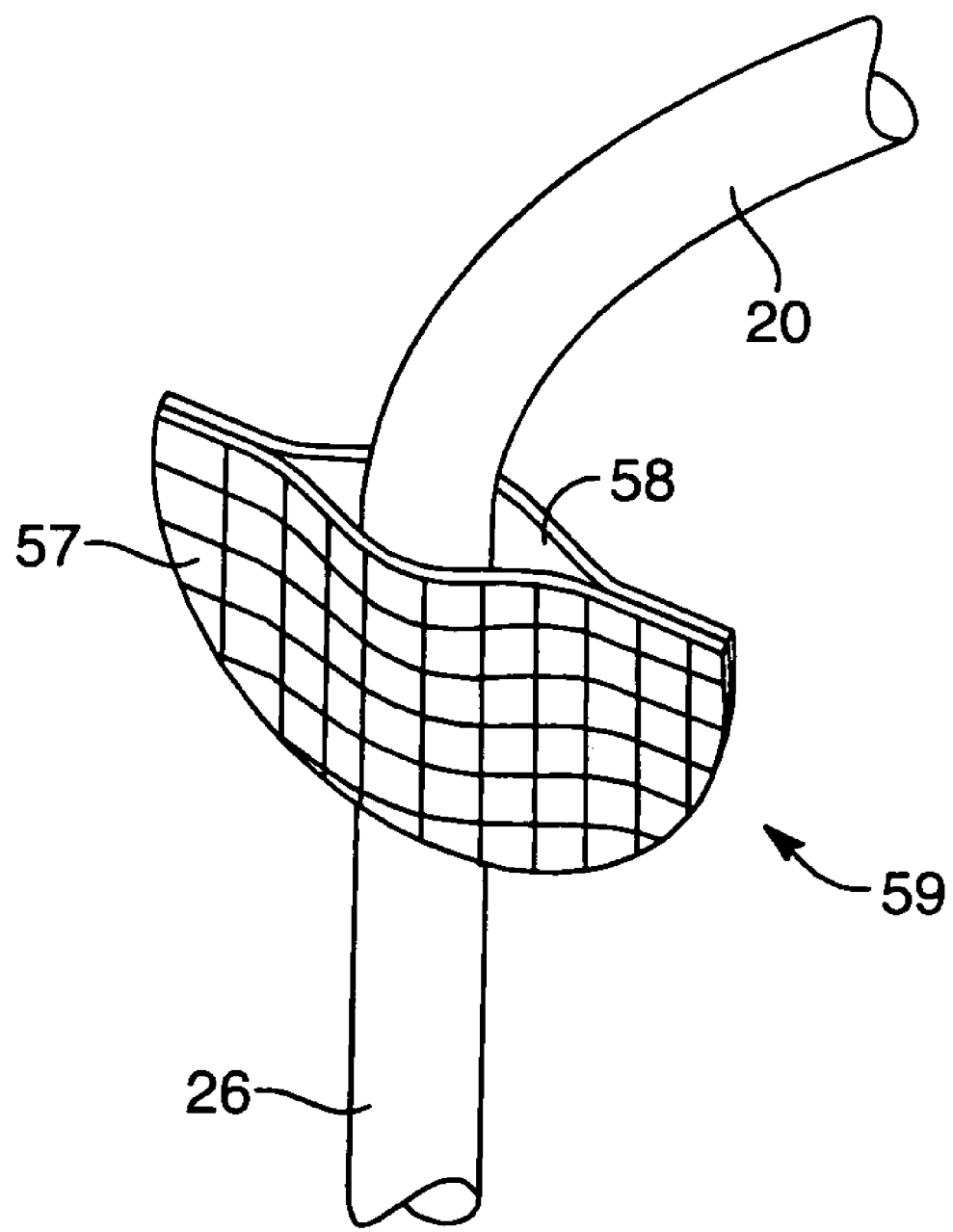
FIG. 10 is a perspective view of one embodiment of a suture material presented in an implant device, and illustrating a local reinforcing member for accommodating and redistributing localized stresses induced by the suture.

Referring to FIG. 10, with or without the presence of a mesh 52, a layer 57 and a layer 58 of a reinforcing material 59 may surround a suture 20 near the location where the suture 20 extends from the backplate 18. For example, in the illustrated embodiment, the suture material 20 may extend from an embedded portion 26 or anchor portion, through a reinforcement 59 defined by two layers 57, 58 enveloping the suture. Accordingly, the reinforcement 59 may be formed of a mesh, a film, or any suitable material calculated to distribute stress into the backplate 12 or other portion of the apparatus 10.

In one embodiment, the reinforcement 59 may actually be embedded partly within the backplate 12 or other portion of the apparatus 10, and extend partly away therefrom in order to receive the suture 20 therethrough. In yet another embodiment, the entire reinforcement 59 may be embedded within the backplate 12 or other portion of the apparatus 10, leaving only the suture to extend from the periphery of the apparatus 10 for access by a surgeon.

As a practical matter, a single strand of suture 20, may provide a very high localized stress capable of ripping, shearing, rupturing, or otherwise damaging the mechanical integrity of the apparatus 10. Accordingly, a reinforcement 59 may redistribute stress between the suture 20 and the underlying material of the apparatus 10.

Figure 11:
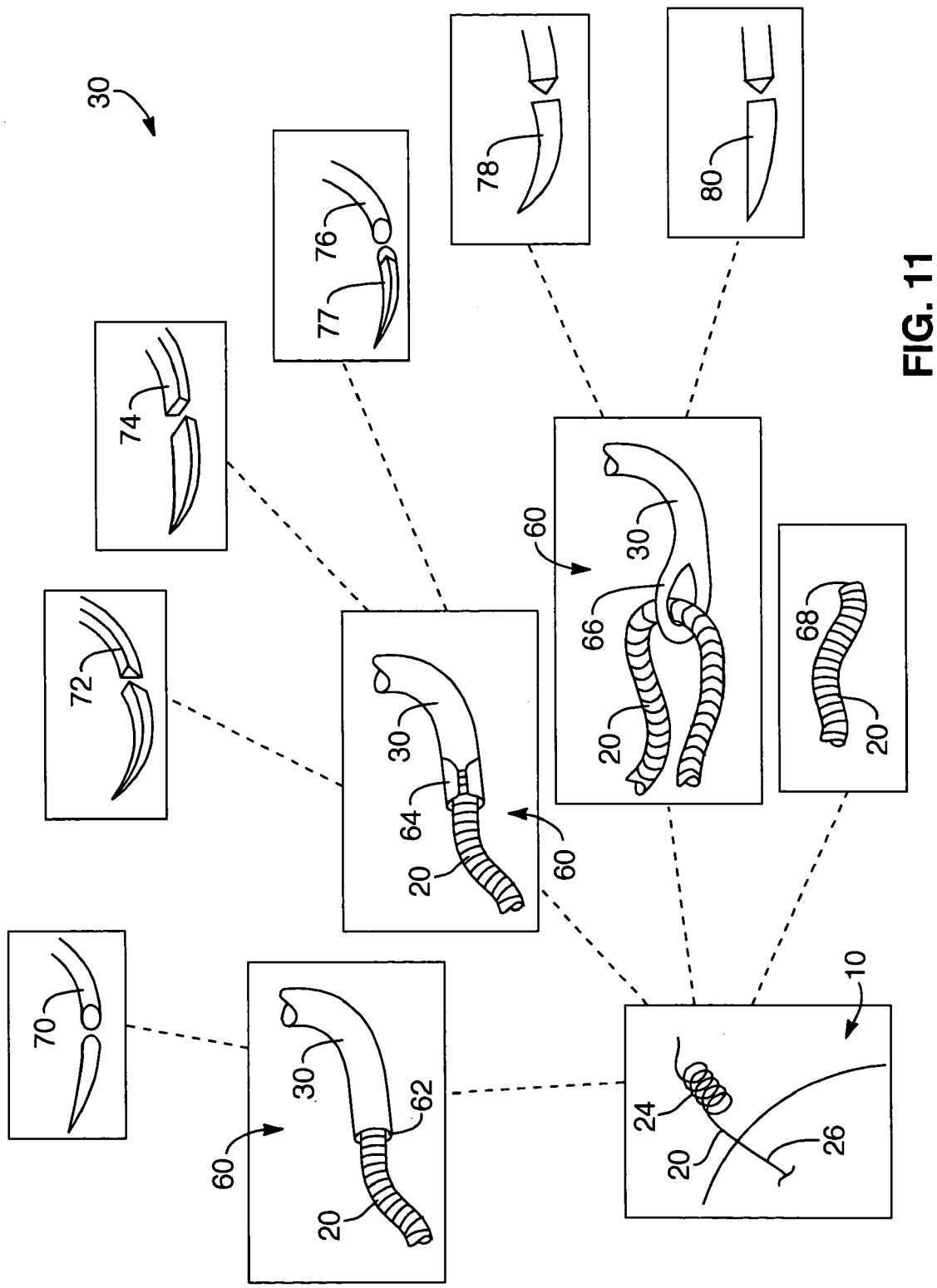
FIG. 11 is a perspective view of various embodiments of needles, connections to sutures, and points of needles for use in an apparatus and method in accordance with the invention.
Figure 12:
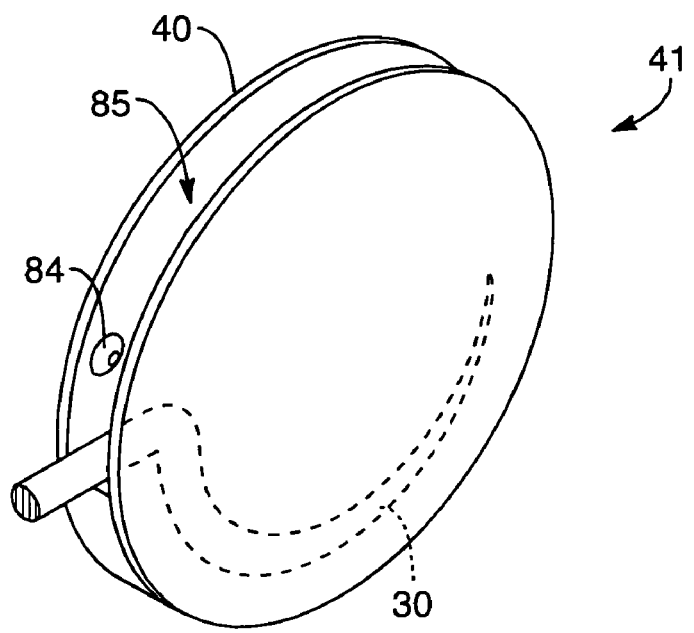
FIG. 12 is a perspective view of one embodiment of a protection device for hiding a point of a suture needle embodied in an apparatus in accordance with the invention.

Referring to FIG. 11, the apparatus 10 may include an embedded portion 26 or enclosed portion 26 of the suture 20. The suture 20 extending therefrom may include a coil 24 or extra length 24 of suture material 20 to be used by a surgeon in anchoring the apparatus 10 to the chest wall, muscle tissues, or the like of a subject (patient).

The connection scheme for connecting the suture 20 to a needle 30 may include one of a variety of techniques. In one embodiment, bonding or glueing the suture 20 into a cavity 62 drilled, cast, or otherwise formed within one end of the needle 30 may form a suture connection 60 that is comparatively seamless. This provides no exposed edges to snag tissues or inhibit easy passage of the needle 30 during suture.

In an alternative embodiment, a suture connection 60 may be formed by having a roll end 64 or tabs 64 crimped to hold the suture 20, by a combination of friction, distortion, or the like, to the needle 30. The tabs 64 or the crimp 64 may present a change in cross-sectional area of the needle 30, thus providing a source for snags, and resistance to passage of the needle 30 through tissues.

Yet another alternative embodiment may be more classical, providing an eye-end 66 to receive the suture 20. In this embodiment, the needle 30 appears much like a conventional needle. Although having a point, shape, and material suitable for surgical use, rather than conventional fabric use, this is independently threaded at the time of use. In this embodiment, the suture 20 may be simply left with an open-end 68 to be threaded through a needle 30 of choice. Alternatively, the open-end 68 may be bonded at the time of use. Nevertheless, in certain embodiments, surgeons prefer to have a previously attached needle 30 securely bonded or otherwise fastened to a suture material 20 for immediate use.

As a matter of convenience, surgical needles 30 are often formed as a substantially semi-circular arc. The various needles have geometry suitable to their specific function. Suture needles 30 may be, for example, formed with a taper point 70, a round bodied needle used for organ tissues, intestines, and the like.

In certain embodiments, including attachments through bone and the like, a reverse cutting needle 72 or a cutting edge needle 78 provide a cutting edge on at least one corner of a typically triangulated cross-section. In an alternative embodiment thereof, a tapered needle 76 with a cutting point 77 in combination therewith may provide a hybrid device 30.

Other specialized needles, including a spatula point 74, and a straight point 80 that does not provide the typical semi-circular needle 30 are alternative embodiments. A taper cut needle 76 is typically used for anchoring to skin, mucosa, muscle, and tendon materials. Cutting needles 78 and reverse cutting needles 72 provide cutting ability, whereas a taper point mechanically tends to stretch tissues therearound. Accordingly, a cutting point 72, 78 may rely upon subsequent scarring to correct its effects, whereas a round point 70 may rely more on the resilience and displacement of tissues to accommodate the trauma and aperture formed therethrough.

Given the very sharp points and edges present with needles 30, a sheath 41 may fit around a needle 30. For example, in one embodiment, the sheath 41 may be formed as a clip 40 having detents 84 to clip the needle 30 into the sheath 41 securely. Nevertheless, the detent 84 may be formed as a simple knob 84 that can be easily deflected by a surgeon in withdrawing the needle 30 from the sheath 41. Similarly, detents 84 may be placed in more than one location in order to substantially fix a needle 30 with respect to the sheath 41 until withdrawal for use. By shaping the sheath 41 as a circle, or button, the sheath 41 may actually contain the coil 24 or excess length 24 of suture material 20. Thus, the sheath 41 may simply form a button extending from the back plate 12 of the apparatus 10 at insertion.

After proper location of the apparatus 10 with respect to the physiology of the patient, a surgeon may then unclip the suture material 20, 24 along with the needle 30 from the sheath 41 for use. The sheath 41 may be formed of a comparatively stiff yet flexible material, such as polyethylene, polyester, polypropylene, or other suitable materials. Since the material of the sheath 41 will not be left within any body cavity, the material need not be subject to the same scrutiny and physiological properties as those of the suture 20 or the apparatus 10 remaining in a patent.

Figure 13:
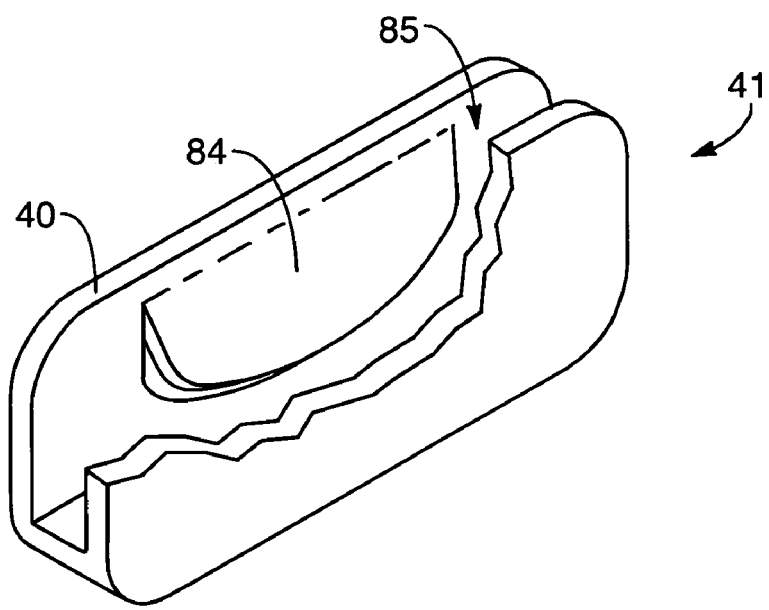
FIG. 13 is a perspective view of one embodiment of a cover for a suture needle for use in an apparatus in accordance with the present invention.

Referring to FIG. 13, an alternative embodiment may be more of an oval or rounded rectangular shape having a detent 84 to receive and retain a needle therearound. An aperture or slot shaped to receive the needle may also be sized to receive the extra suture material 24. The shape may be rounded, rectangular, or the like, but sharp edges tend to snag, drag, and otherwise resist easy positioning. Accordingly, corners may be rounded, and materials selected to have flexibility. For example, the sheaths 41 may actually be formed of a material that is merely a stiff elastomeric material such as a rubber, latex, silicone, or the like. With proper thicknesses and other dimensions (e.g. length, width, diameter), the sheaths 41 may serve their purposes adequately. They may still be highly flexible and capable of substantial distortion in order to open to release the needle 30, suture material 20, or both.

Figure 14A:
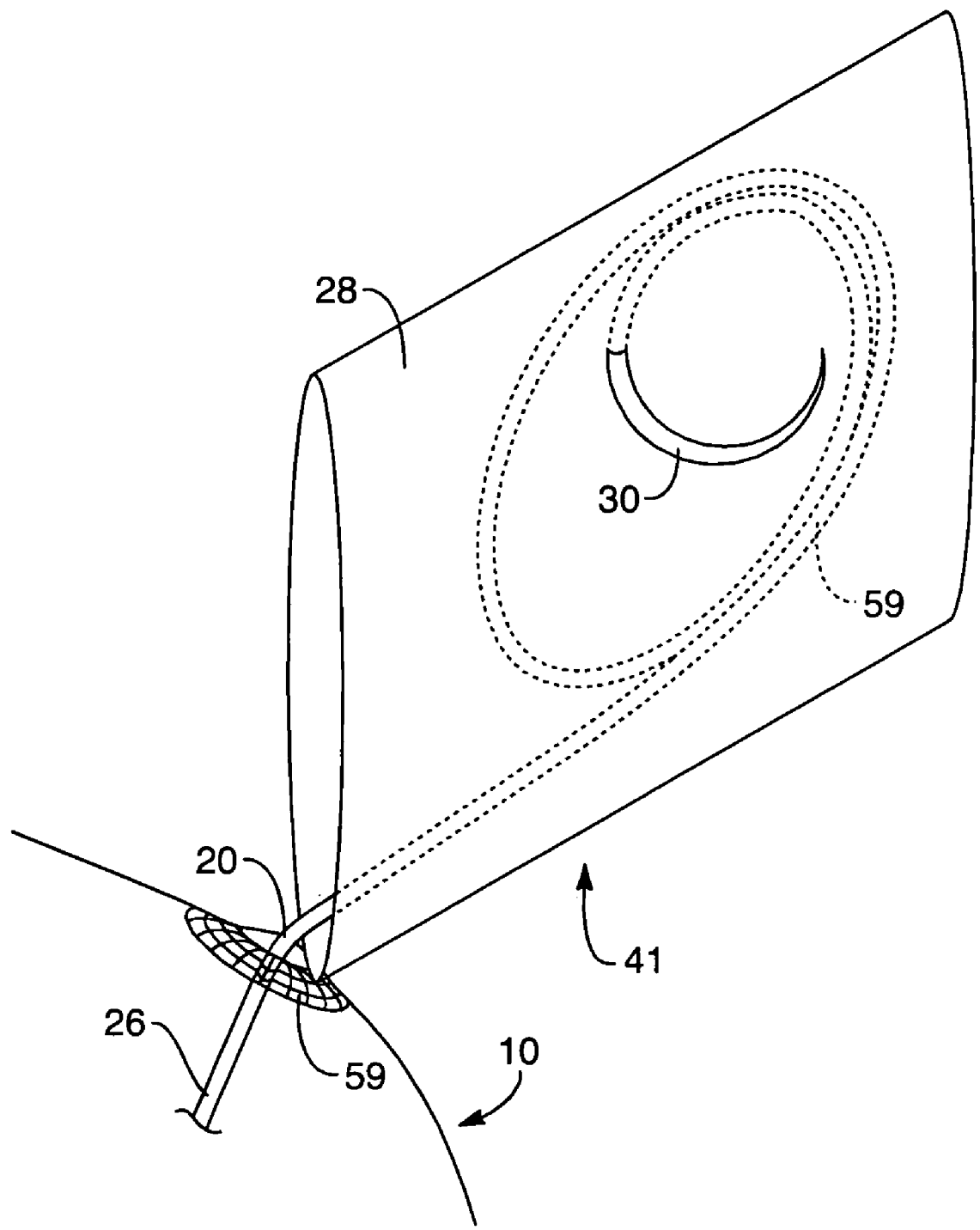
FIG. 14A is a perspective view of one embodiment of a protective envelope for a suture and needle in accordance with the invention.

Referring to FIG. 14A, a sheath 41 may be embodied as an envelope 28 formed of any suitable material. The material may be a paper, polymeric paper, plastic, comparatively rigid, stiff, flexible, elastomeric, or the like. In one embodiment, the suture material 20 is simply coiled up as extra material 20 connected to a needle 30 all inserted into the envelope 28.

The protective sleeve 28 or envelope 28 may be positioned close to the apparatus 10, even in very close proximity to the reinforcement 59. The suture 20 may be taped, glued, crimped, clamped, or otherwise secured against easy slippage with respect to the envelope 28 in order to provide ease of working while placing the apparatus 10 physiologically. Thereafter, a tug, clip, cut, tear, or the like from a surgeon using scissors, forceps, scalpel, needle, or the like may release the envelope 28 for removal. Thereupon, the needle 30 becomes accessible with the suture 20 including the entire coil 24 of extra material 24.

Figure 14B:
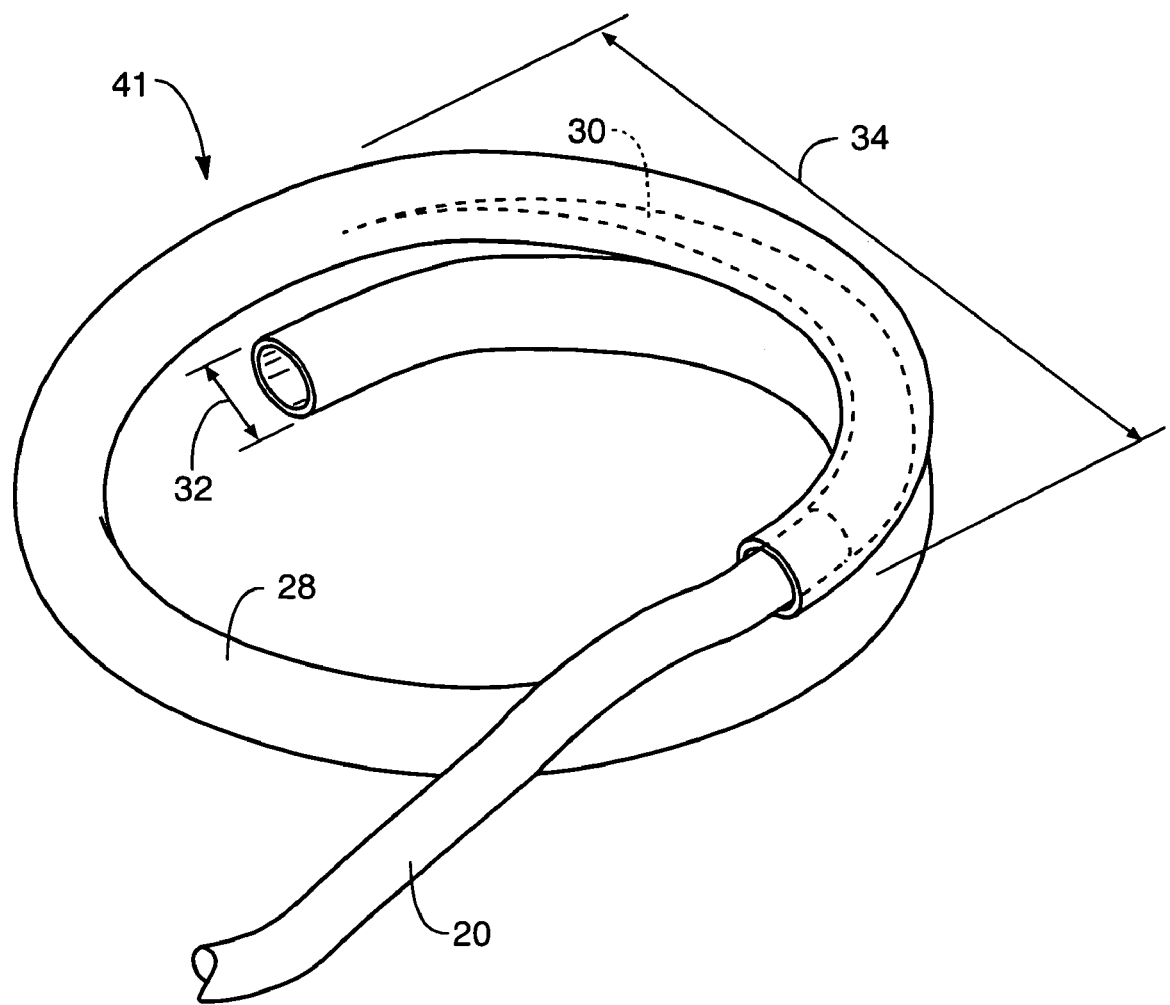
FIG. 14B is a perspective view of a coiled-tube protective cover for a needle in accordance with the invention.

Referring to FIG. 14B, one alternative embodiment may include a sheath 41 formed as an envelope 28 or a coil 28 of a tubular material having a diameter 32 suitable for receiving a needle 30. The sheath 41 may extend, for example, through 360, 540, 720 or more degrees of the coil 28. Space between adjacent loops or turns of the coil 28 may close, spring-like, to hold suture materials, clip to a substrate, or the like. Meanwhile, the needle 30 may be extracted from the interference fit within the inner diameter 32 of the tubular material of the coil 28. Likewise, the coil 28 forms a diameter 34 that operates much like the button concept of FIG. 12. Thus, the sheath 41 as a coil 28 operates as a small medallion or loop that resists snagging with respect to tissues coming in contact therewith.

Figure 15:
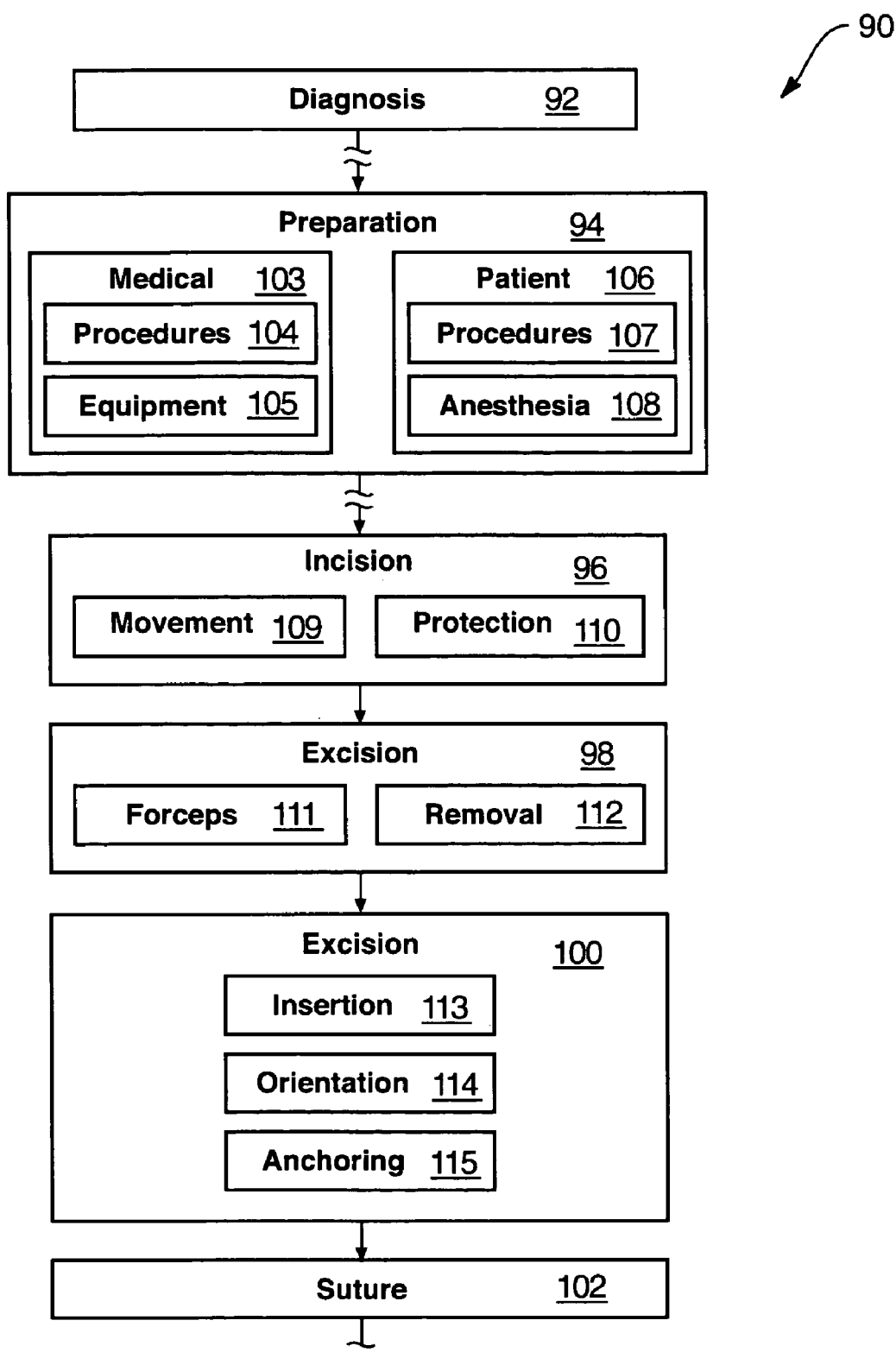
FIG. 15 is a schematic block diagram of a mastopexy process including insertion, orientation and anchoring in for an apparatus and method in accordance with the invention.

Referring to FIG. 15, a process 90 for implementing an apparatus and method in accordance with the invention may be given the diagnosis 92 of a condition. The condition is typically referred to as ptosis. In a ptosis condition, stretching of tissues under the influence of physiological expansion followed by subsequent internal tissue shrinkage, the effects of gravity over time, and the like may cause displacement or discomfort. This condition is usually characterized as skin drooping and lack of fulness in underlying tissues. Accordingly, a mastopexy operation relocates selected tissues, excises certain tissues, and reconnects with sutures the remaining tissues in a new geometric configuration. An apparatus 10 may augment the lack of fulness remaining. The process is often times called a mastopexy or a lift.

At some point following diagnosis 92, preparation 94 occurs. Medical preparations may include preparations of a patent, procedures 104, and equipment 105, including selection and preparation of the apparatus 10 for an operation. In addition, the patient preparation 106 may include specification or selection of procedures 107, as well as study and practice thereof, along with anesthesia procedures 108. In addition, other common preparation procedures may be employed. Some of those procedures include standard antiseptic and field preparation procedures, as well as informational procedures for patents, doctors, staff, and the like.

A significant part of preparation 94 will be selection of corresponding procedures 104 and equipment 105 consistent with the apparatus 10. In any operation involving the use of the apparatus 10 in accordance with the invention, the procedures 104 appropriate thereto will be selected after study, and studied after selection. Similarly, selecting an anesthesia 108 may involve determinations of whether an operation is to be conducted under local or general anesthesia. Typically, mastopexies are conducted with general anesthesia. By contrast, some augmentation procedures require sufficiently noninvasive processes that local anesthesia may be adequate. Similarly, localized anesthesia with some degree of sedation short of unconsciousness may also be selected. Eventually, during preparation of a patient, anesthesia will be applied. Shortly after application of anesthesia 108, incision 96 will begin.

The incision process 96 may involve certain standard and certain new procedures in accordance with the invention. Typically, the broad classes of incisions are part of opening the actual region subject to surgery, and excising tissues to be removed. Incisions will include the process of cutting free and moving certain tissues. For example, movement 109 of the entire mammary duct system in a superior direction, may not be possible. Nevertheless, the majority of ducting, along with terminations in the areola and nipple will be moved in their entirety. Nevertheless, as a natural consequence of subsequent excision 98 of certain tissues therebelow, some ducting may be excised.

As a practical matter, protection 110 of tissues will be required, including hydration, standardized surgical procedures, including clamping off vessels, and the like. Typically, irrigation, cleaning, suction, and the like may be used to maintain the area clean and clear for observation and navigation by the surgeon. Further details regarding the incision processes and locations will be described hereinafter.

Excision 98 typically involves connecting forceps 111 or a hemostat 111 to literally tag tissue and provide a handle for manipulating it. Hemostats are often used to close off vessels, but may also be used as handles to identify and manipulate tissues to be removed. Upon completion of the necessary incisions 96, removal 112 may include an incision separating removed tissue from the surrounding area. The details of excision locations and tissues will be described hereinafter.

Implantation 100 involves insertion 113 of an apparatus 10. That is, mastopexy processes may be with augmentation or without augmentation. Since mastopexy involves relocation and reshaping of the physiology of a patient, augmentation may or may not be required or advisable. In the event that augmentation is deemed appropriate for purposes of enhancement or to provide or restore symmetry, an insertion 113 of an apparatus 10 places the apparatus 10 within an incision underlying the glandular structure, the muscular structure, or both of the patient. Subsequently, tissues will heal around the apparatus 10, on the periphery of the incision.

Following incision and insertion 113 of the apparatus 10, orientation 114 may occur in each axial, and some rotational directions. For example, the apparatus 10 should be oriented in the superior-inferior direction or along a superior-inferior axis in order to provide the effective lift effect at the proper location. Thereafter, the apparatus 10 for a second breast needs to be oriented in the superior-inferior direction with respect to the initial implant 10. Likewise, each implant apparatus 10 needs to be oriented in a lateral-medial direction in order to provide the desired effect, and needs to be arranged in the instance of the second breast to be symmetric along both lateral-medial axes and superior-inferior axes to provide desirable symmetry.

Moreover, to improve the longevity of the effect or of the mastopexy procedure, anchoring of the apparatus 10 by way of sutures 20 may reduce the effects of gravity as an agent causing damage during healing, extension of healing, capsular scar thickening, and the like. Thus, a surgeon may use the suture 20 to anchor the apparatus 10 to the chest wall, through cartilage in the chest wall, through ribs in the chest wall, or the like. In this event, the orientation may be made with respect to a rib, in order to place both tabs 18, or both sutures 20 in close proximity to a single rib.

Thus, the apparatus 10 may actually be rotated about an axis substantially perpendicular to the back plate 12 in order to properly orient the anchor points in accordance with the actual physical anatomy of the patient. Thus, the ease, durability, and equality of sutures is maintained. That is, if both sutures 20a, 20b are placed through the same edge of the same bone, or through the same region of cartilage between the same pairs of ribs, then the sutures should be expected to behave substantially equally in supporting the apparatus 10 in use. Similarly, if inferior tabs 46 or inferior sutures 30c, 30d are used, they may be similarly and symmetrically oriented with respect to one another.

Typically, in an apparatus and method in accordance with the invention, anterior-posterior orientation is not a problem. Typically, geometry of the back plate 12 and the orientation with respect to either tabs 18 or sutures 20 integrated with the back plate 12 will provide immediate, visible, and tactile assurance of the anterior-posterior orientation. Likewise, superior-inferior rotation can easily be detected by the same visible indicia.

By contrast to many augmentation procedures and devices, the apparatus 10 used in a mastopexy procedure is not substantially hidden from the surgeon. That is, a peri-areolar incision may be very small, and an implant may actually be rolled up and unfilled at the time of insertion in augmentation surgeries. By contrast, in mastopexy, due to the nature of the incisions 96 and excisions 98, the implant region is typically visible and accessible for suturing, and orientation is not inherently problematic.

Anchoring 15 may involve a variety of processes, apparatus 10, tabs 18, sutures 20, and the like. As discussed hereinbelow, anchoring 115 after orientation 114 of an apparatus 10 assures two major advantages over prior art systems. The apparatus 10 is anchored 115 against the effects of gravity, physical motion, and the like during healing. Accordingly, the edges or periphery of incisions 96 are protected immediately against incursion, pressure, forces, and the like from the apparatus 10 in any direction against which sutures 20 have been made. Thus, gravity cannot urge the apparatus 10 to move substantially into tissues to expand scarring, or exacerbate or inflame an incision.

If lower tabs 46 or inferior sutures 30c, 30d are used, physical activity will be inhibited from causing motion in a superior direction. Meanwhile, the selected location of the tabs 18 or sutures 20 embedded in the apparatus 10 provide both lateral-medial migration resistance, and superior-inferior migration resistance due to physical activity or the natural effects of gravity. In addition to support during healing, permanent suture anchors may provide permanent support against all of the foregoing forces that might tend to displace the apparatus during a long term.

Following implantation 100, suturing 102 closes up all exposed incisions. This implies suturing closes the capsule or capsular volume enclosing the apparatus 10. Likewise, closing all skin incisions in order to reform the exterior of the breast will complete relocation of the areola region and closure of the inframammary boundary or incision, as well as the midline or medial incision therebetween.

Figure 16:
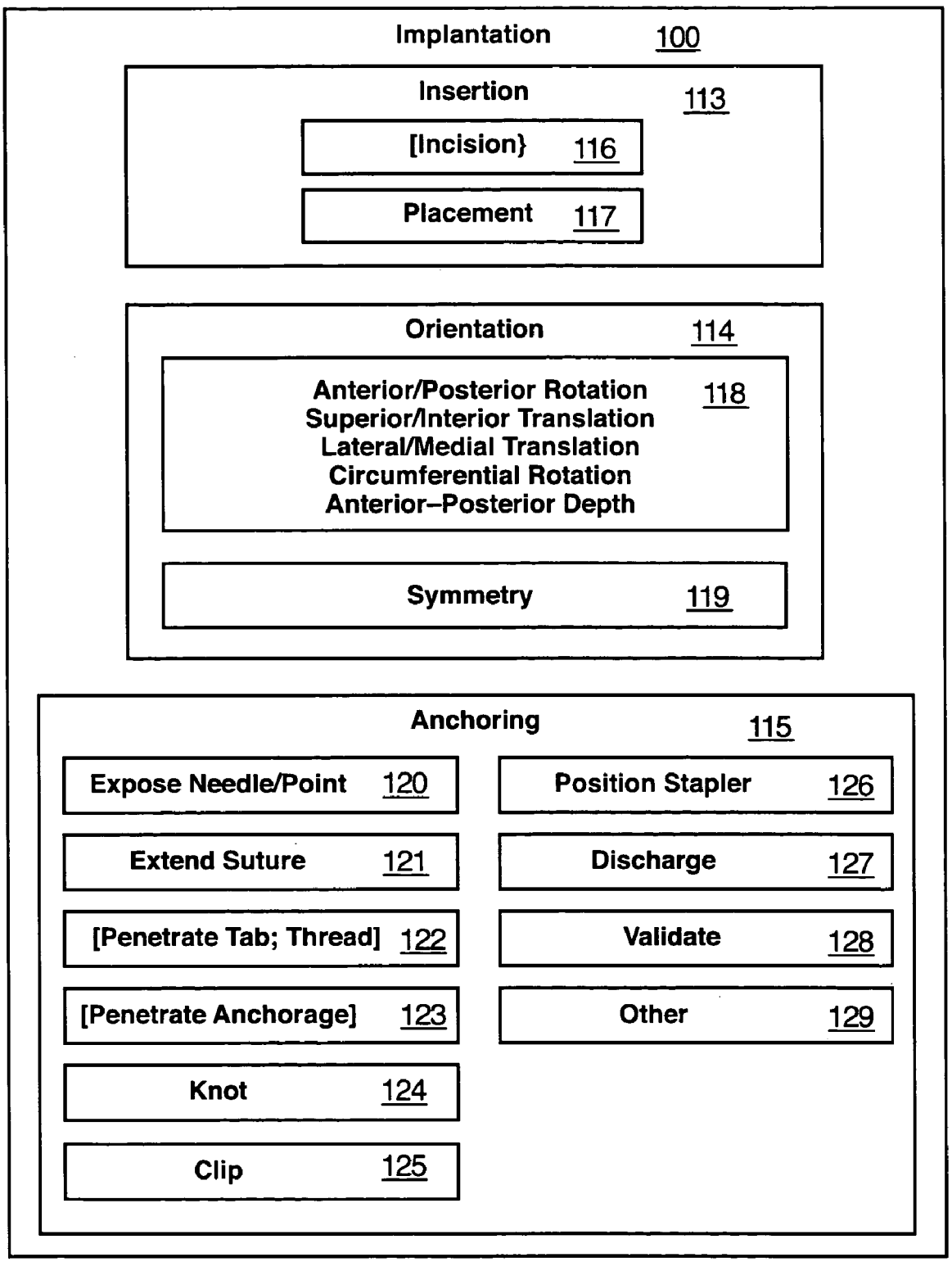
FIG. 16 is a schematic block diagram of the implantation process of FIG. 15.

Referring to FIG. 16, implantation 100 may include insertion 113, orientation 114, and anchoring 115. During insertion 113, an optional incision 116 may be transaxillary (under the arm) but is typically inframammary. The implant 10 may be placed under the muscle (submuscular, under the pectoralis major), or may simply be subglandular (outside of the main pectoral muscle group, and below or within the skin and mammary tissues).

In addition, the incision 116 may actually be made laparoscopically. That is, a laparoscope or a long flexible tube containing various tools, vision apparatus, lighting devices, instrument insertion tubes, and the like may be inserted in order to minimize trauma. In other processes, the entire tissue structure may be opened up by broad incisions to provide ready access to all tissues involved.

Placement 117 typically involves positioning the back plate 12 against the muscles or wall of the chest. Orientation 114 may include orientation to assure against accidental rotation either anterior/posterior or superior/inferior. Similarly, lateral/medial rotation may occur, but is effectively anterior/posterior rotation. Some implants are anatomically shaped, while others are merely hemispherical. In a situation with a hemispherical implant, anterior/posterior rotation produces the same effect as lateral/medial or superior/inferior rotation.

Orientation may include superior-inferior translation in either direction or lateral-medial translation in either direction. Circumferential rotation about an axis substantially perpendicular to the back plate 12 may be used to orient the tabs 18, sutures 20, or both in accordance with the body physiology in order to optimize the location, symmetry, and loading of anchoring.

Anterior-posterior depth 47 may be adjusted in some implants 10 by a surgeon. Other implants 10 are manufactured with a particular volumetric content. Thus, optionally, a surgeon may select the anterior-posterior depth 47 of an apparatus 10.

Symmetry 119 may involve all of the orientation factors 118. However, the orientation factors 118 apply to both implants with respect to themselves, one another, and with respect to the overall anatomy of the body of a patent.

Anchoring 115 may include a variety of optional processes. For example, exposing 120 a needle 30 or the point thereof may be required as a separate step if certain sheaths 41 are provided. Otherwise, a needle 30 may simply be selected for use with a suture 20 provided independently therefrom.

Extending 121 the suture material 24 or the suture 20 from a packet, envelope, or other sheath 41 may be required in a case of a suture 20 and needle 30 integrated with an apparatus 10. In an alternative embodiment, the suture 20 may be provided in a separate package and may be withdrawn 121 or extended therefrom.

Penetrating 122 a tab or threading 122 a needle 30 is considered an optional step or optional steps 122. That is, threading a needle 30 is often not required in an apparatus and method in accordance with the invention when the suture 20 is previously bonded to a needle 30. This is particularly true when embedded or otherwise integrated with an apparatus 10. Likewise, tabs 18 may or may not be provided with an apparatus 10. Accordingly, penetrating 122 and threading 122 are optional steps that may or may not be required in a particular embodiment in accordance with the invention.

Penetrating 122 the anchorage involves the penetration by a suitable device, such as a needle with trailing suture 20, of the tissues that will provide the anatomical support for the apparatus 10. Penetrating 123 may involve passing a needle 30 through bone, cartilage, or the like in the chest wall. Similarly, penetrating 123 may involve passing the needle 30 and the trailing suture 20 through the chest muscle instead. Other anchoring locations may be provided in the anatomy according to the needs of a particular patient. Moreover, an apparatus and method in accordance with the invention may be shaped and anchored in a manner to augment any suitable area of the body. Thus, any region of the body to be aided by prosthetic augmentation can receive a suitably shaped implant appropriately anchored.

Ultimately, knotting 124 the suture 20 provides a degree of permanence to the suture process 102. Excess material from the suture 20 will be clipped 125 and discarded.

In an alternative embodiment, the apparatus 10 may be anchored by stapling rather than suturing 102. For example, positioning 126 a stapling device and discharging 127 a staple through a tab 18 may secure the apparatus 10 to a chest wall, rib, or other part of the anatomy. Ultimately, validating 128 the stability of a suture process 102 or another anchoring process 115 is advisable to assure that neither non-anchored apparatus 10 nor inadequately or partially anchored apparatus 10 result from the process 100.

Anchoring 115 provides a number of benefits in accordance with the invention. In the situation involving axially symmetric, hemispherical apparatus 10, a surgeon may desire to find anatomical symmetry along a line, about a point, and with respect to both implants 10 inserted 113. Precision in location relative to the patent's anatomy, as well as symmetry with respect to one another may be achieved with a degree of reliability by providing anchoring 115 as part of the process 100.

Biological tissues do not necessarily react or respond exactly as inanimate materials and machines do. The body will react and respond to the mastopexy process. Accordingly, the process 100 does not last forever. To accommodate the natural decline of resilience and fullness of tissues, a surgeon may "overlift" by positioning a device 10 higher than ultimately expected or desired. Accordingly, over time, the natural reaction of tissues to the presence of the apparatus 10 may result in a shift in the inferior direction.

However, because the apparatus 10 in accordance with the invention provides anchoring 115 as part of the implantation process 100, overlifting is not required. The anchor provides a degree of certainty as to the location of the apparatus 10. Likewise, exactly locating the apparatus 10 along any lateral-medial axis is possible. Accordingly, the process 100 provides a comparatively broad tolerance for a surgeon in completing the operation 100, and yet results in a comparatively fine tolerance in the result, the ultimate location of the apparatus 10 with respect to the patient's anatomy.

As discussed hereinabove, forces may arise from sleep, physical activities, athletic pursuits, accidents, and the like. Moreover, the weight of a patient may change over time either up or down. Accordingly, anchoring 115 provides a degree of assurance of proper location with respect to the body structures, rather than permitting a migration or shift with tissues, gravity, scarring or as a result of the reaction of tissues to the presence thereof.

The concept of dynamic rippling or wrinkling arises from a wave motion, natural in liquids, unnatural in solids. Ripples due to waves in implant filler materials may be visible through the skin. Rippling may be reduced to a certain extent by the presence of anchoring. That is, anchoring an apparatus 10 provides a node that is not subject to substantial displacement. Thus, a wave node necessarily affects and limits the propagation of dynamic waves, particularly in inviscid fluids used as fillers in the apparatus 10. Thus, the characteristic dynamic ripple may be reduced or even eliminated in some case by suitable anchoring 115.

Thus, one can see that a degree of simplicity, reliability, reduction of side effects, scarring control, and reduced scar stretching are provided by virtue of both the temporary and permanent support of the anchoring process 115 controlling the physiological location of the apparatus 10. Accordingly, rather than the considerable scarring, stiffness, and capsular contracture experienced in prior art devices, reduced scarring and inflammation can be expected, as well as stabilization against migration.

Figure 17:
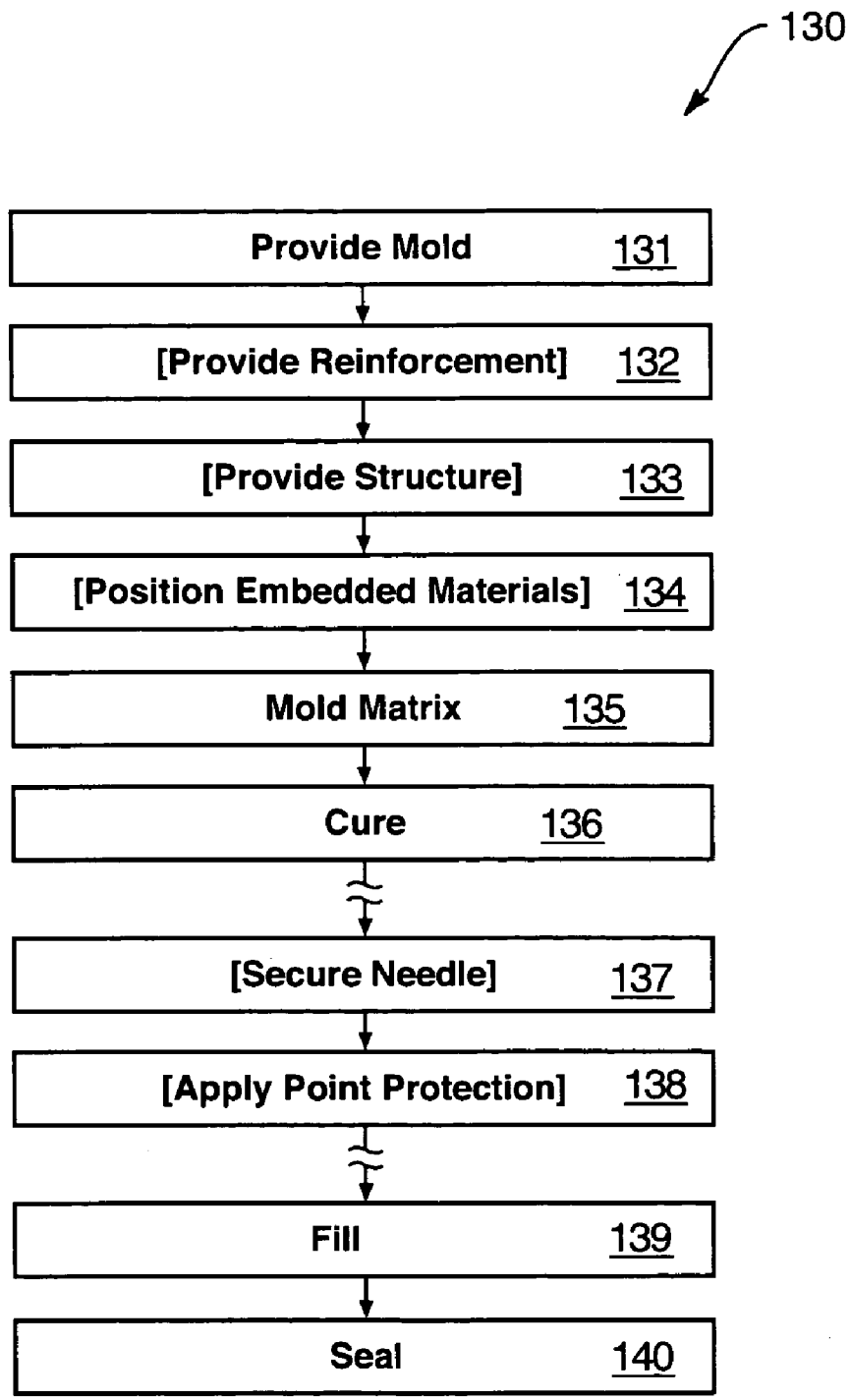
FIG. 17 is a schematic block diagram of one alternative embodiment, and illustrating various alternative and optional steps therein, for manufacture of an apparatus in accordance with the invention.

Referring to FIG. 17, a process 130 for manufacturing an apparatus 10 in accordance with the invention may include providing 131 a mold shaped to produce one or more portions of the apparatus 10. For example, in one embodiment, a roto-molded apparatus 10 may be formed in a closed mold fitted and smoothed to provide substantially no seam lines, flash, or the like. Roto-molding and injection molding are well understood in the plastics manufacturing industry. In other embodiments, the apparatus 10 may be fabricated by vacuum forming, blow molding, or the like using suitable elastomeric or polymeric materials. For example, dimethyl-siloxane (e.g. SILASTIC™ Dupont) has been found to be a moderately low-temperature vulcanizing material suitable for molding.

Providing 132 reinforcement 48 by way of fibers, whether random, oriented, angled, or the like, may enhance the structural integrity and the weight-bearing capacity of an apparatus 10. Similarly, providing 133 sutures 30 may be optional in the manufacturing process. Sutures 30 may be embedded in the back plate 12 or otherwise in the apparatus 10. Sutures 30 may be provided by a surgeon after manufacturing, such as during the actual surgical operation 100.

Positioning 134 embedded materials (e.g. the mesh 50, reinforcing fibers 48, or the like) is also shown in brackets indicating that this step is optional in the process 130. Positioning 134 the embedded materials may not be required if the material of the apparatus 10 is to be completely formed of a single material. By contrast, the back plate 12 may still be homogeneously formed of a composition or matrix 56 embedded throughout a mesh 50. Thus, the result is a substantially homogeneous plate, reinforced by a fiber not homogeneous therewith but uniformly or nonuniformly distributed as appropriate.

Molding 135 a matrix 56 may occur with or without embedded materials 50. Ultimately, however, curing 136 by virtue of temperature change, chemical reaction, or the like may require a period of time, and various chemical or thermal processes. The curing 136 will typically require, or be required in accordance with, a particular chemistry of the base material forming the apparatus 10.

Securing 137 a needle is illustrated as an optional step since a needle 137 may or may not be a part of the apparatus 10. Nevertheless, if a suture 20 is embedded in the material 56 of the apparatus 10, then a needle 30 may be secured 137 to the suture 20 as a practical convenience.

Similarly, applying 138 point protection to the needle 30 is an optional step. Such application 138 depends upon whether or not a needle 30 is present in the apparatus 10 as manufactured. A surgeon may care very much whether or not the needle is protected by application 138 of a sleeve 41 of some type suitable. Needles may be very sharp and can cut tissues or implants with little more than brushing past them.

Filling 139 is a process that will typically occur in any filled apparatus 10. In some embodiments, the fill process 139 may be optional, since the basic material may be a solidus material such as a gel or a foamed solid apparatus 10. However, in an apparatus and method in accordance with the invention, filled apparatus 10 are contemplated in many applications, since they may provide proper weight, sizing adjustability, texture, and other appearance features. The fill 139 or filling 139 of an apparatus 10 in accordance with the invention may involve adding a filler 45 at the time of manufacture, or adding the filler 45 at the time of insertion. Even when the filler 45 is molded or injected into an apparatus 10 during the manufacturing process 130, a surgeon may alter the fill process 139 at the time of the operation 100. Accordingly, the fill process 139 may depend upon whether or not the apparatus 10 does contain a filler 45, and may occur at a time selected by the manufacturer, surgeon, or both.

Ultimately, the apparatus 10 must be sealed 140 against incursion of tissues, or sources of bacteria or infection. Accordingly, the apparatus will typically be sealed against leakage of the filler 45. Atoms and molecules operating within the interatomic or intermolecular distances provided in polymers may actually migrate with respect to one another. Polymers typically constitute long chains that appear like microscopic spaghetti. Accordingly, the effective mesh size or intermolecular distance may actually permit passage over time by shorter chained polymers and single atoms. Accordingly, "weeping" or "microbleeding" of filler materials 45 through the walls of the pocket 14 or back plate 12 of the apparatus 10 are a distinct possibility and probability. Thus, the seal 140 is against the macroscopic passage of materials. Nevertheless, the microscopic passage of materials may actually continue at a comparatively very low flow rate.

Figure 18:
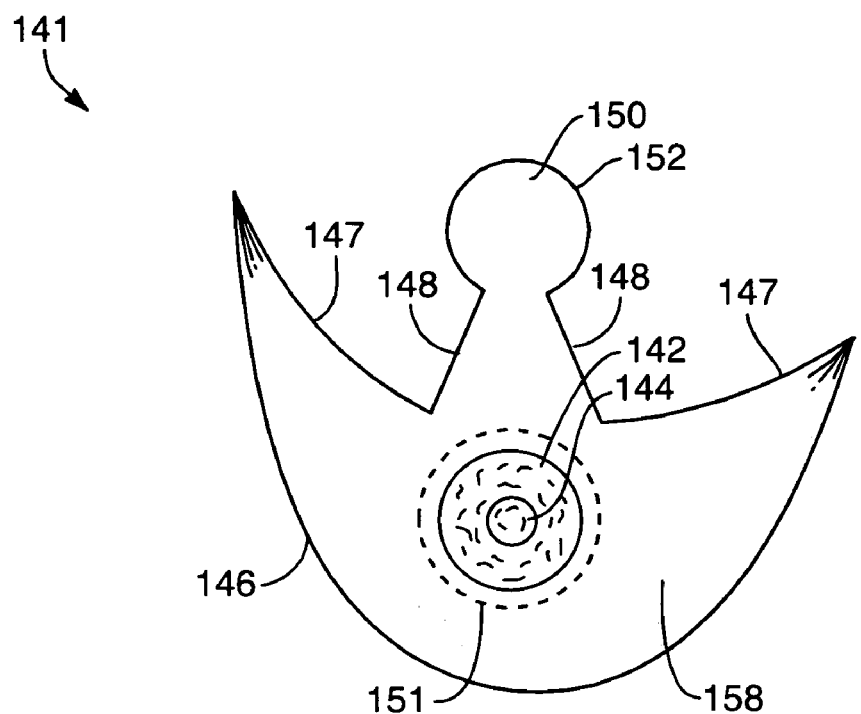
FIG. 18 is a schematic front elevation view of a mastopexy incision pattern in accordance with the invention.

Referring to FIG. 18, a mastopexy incision is made in something of an "anchor shape." Typically, a breast 141 is incised in a shape or along a series of paths (e.g. curves) that isolate the areola 142 and nipple 144 region for removal with the mammary ducting system. An incision along the inframammary border (e.g. fold, boundary, etc.) connects to incisions along a boundary 147 that will eventually be sutured to the inframammary boundary 146. Intervening tissues of skin and underlying tissues will be excised.

Similarly, an incision 148 is formed that will eventually be sutured to form a midline 149, and appears like the shaft of an anchor, while the incisions 146, 147 appear like the flukes of an anchor. Meanwhile, a substantially circular or arcuate region 150 to be excised is defined by an arcuate incision 152 therearound and connecting the incisions 148. Accordingly, the areola tissue 142 will be relocated to the region 150, and sutured in along the incision line 152 or incision arch 152.

Figure 19:
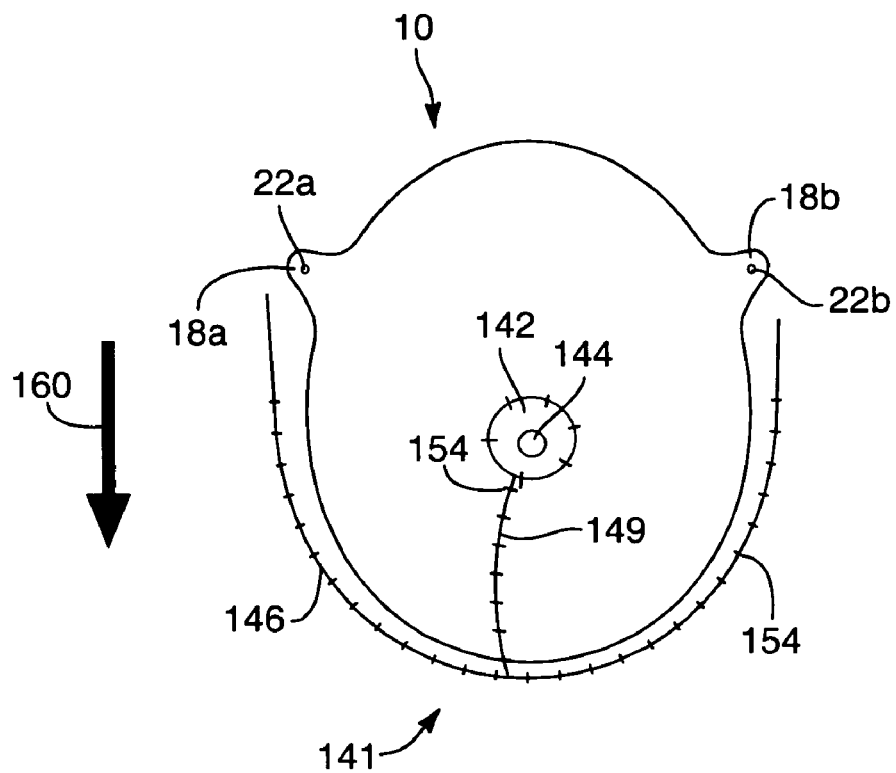
FIG. 19 is a schematic front elevation view of a mastopexy suture pattern in a closed configuration as per an apparatus and method in accordance with the invention.

Referring to FIG. 19, while continuing to refer generally to FIGS. 1–18, the incision 148 is closed to form a midline suture 149 or midline 149, while the incisions 147, 146 are sutured together to form the inframammary boundary 146. A variety of stitches may be used for the various sutures 154 used to close the midline 149 and inframammary boundary 146. FIG. 19 illustrates the comparative positioning in one embodiment of an apparatus 10 in accordance with the invention.

Nevertheless, the tabs 18 may be replaced, or augmented by the presence of the sutures 20 in an apparatus 10 in accordance with the invention. The anchoring of the apparatus 10 resists the temporary and permanent effects of flushes 160 or accelerations 160 due to gravity acting on the apparatus 10 to place forces and pressures on surrounding tissues. Accordingly, the sutures 146, 149 need only sustain the natural mass and weight of enclosed tissues, and not the pressures and forces due to the presence of the apparatus 10.

Figure 20:
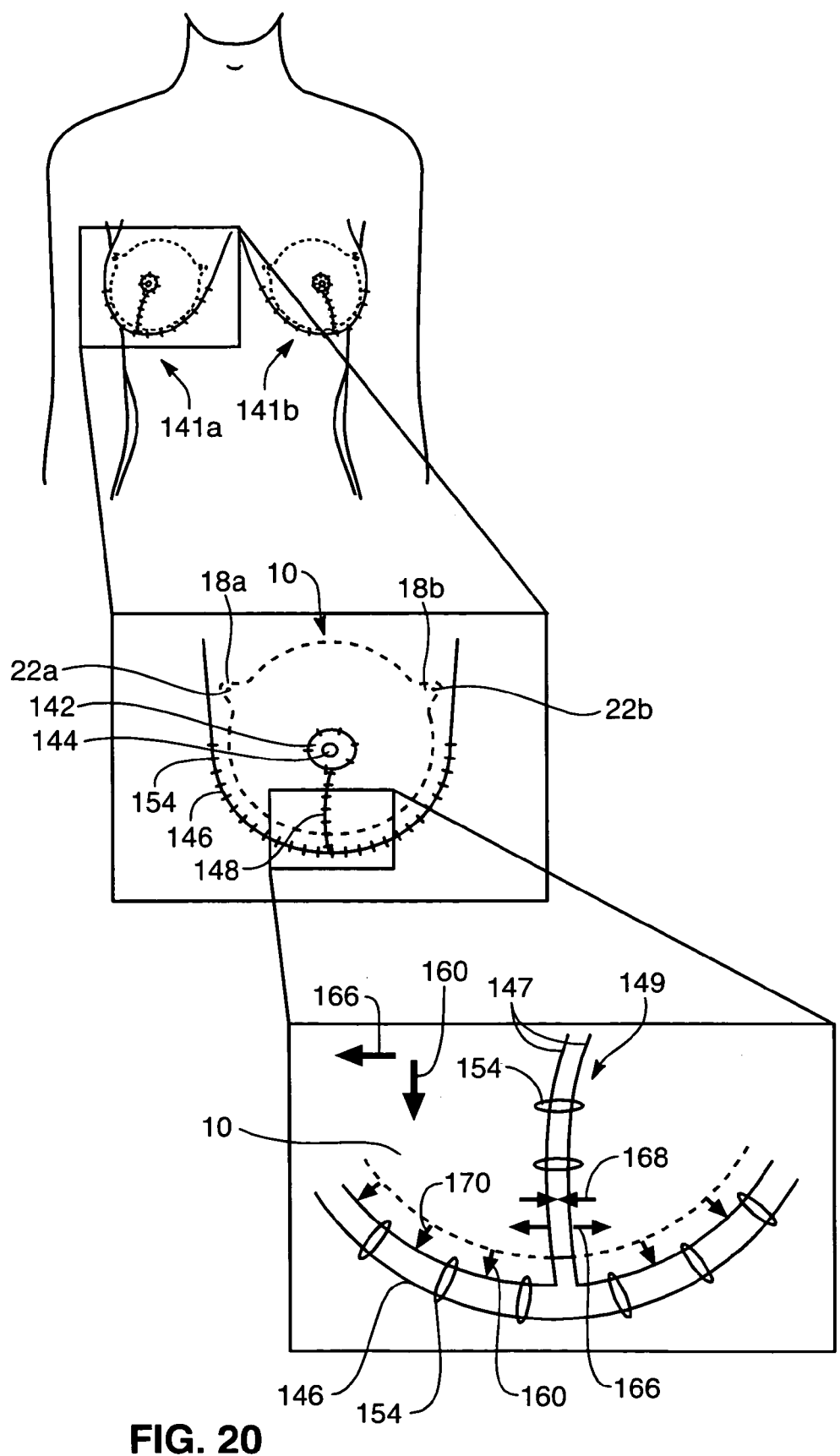
FIG. 20 is a schematic front elevation view illustrating various components of force and pressure exerted, as a result of mastopexy, upon the closing suture to be resisted in accordance with the invention.
Figure 21D:
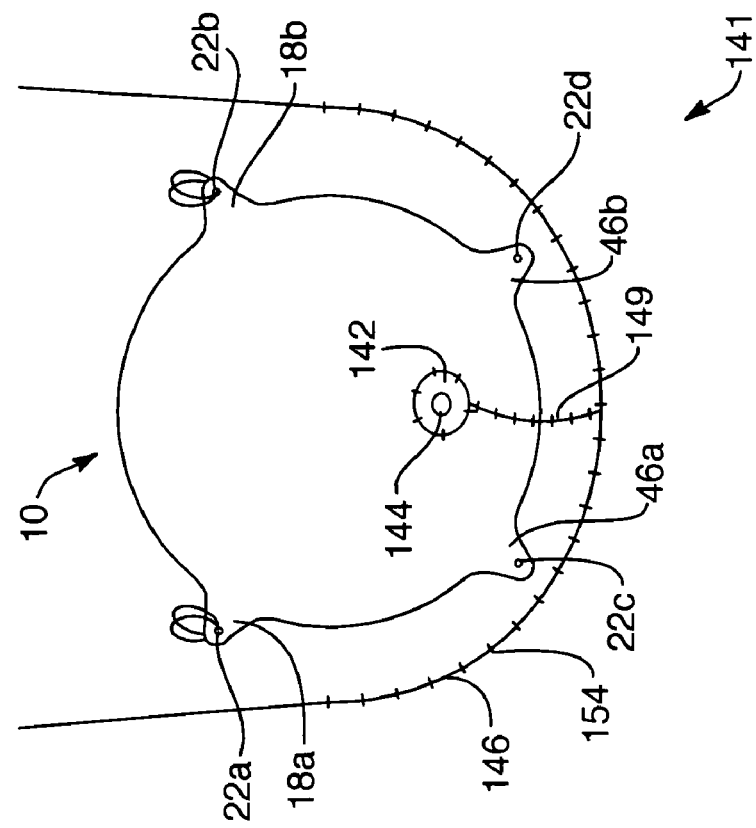
FIG. 21D is a schematic front elevation view of the system of FIG. 21C, wherein FIGS. 21A–21D constitute sub-glandular insertion of augmentation implants.
Figure 21C:
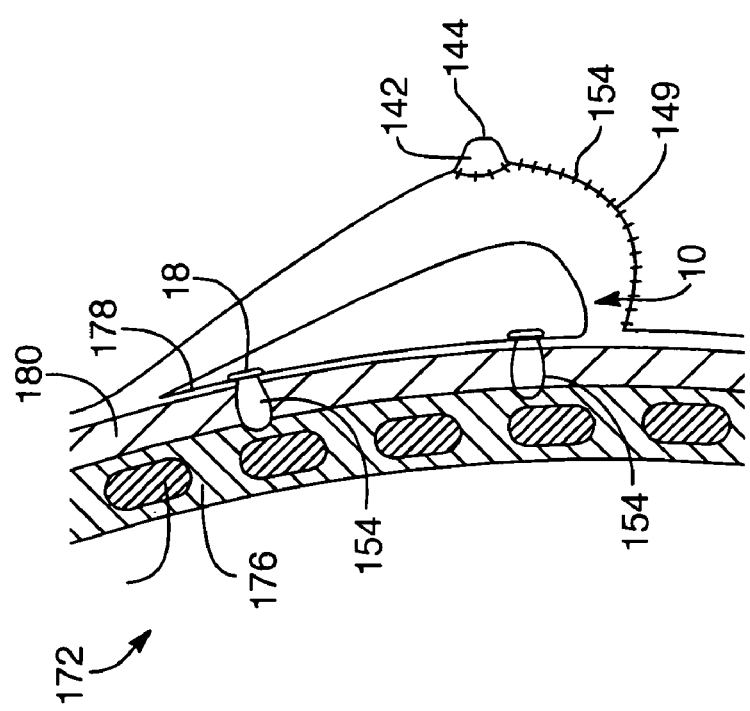
FIG. 21C is a schematic, side elevation, cross-sectional view of an inferiorly and superiorly anchored implant in accordance with the invention.
Figure 22B:
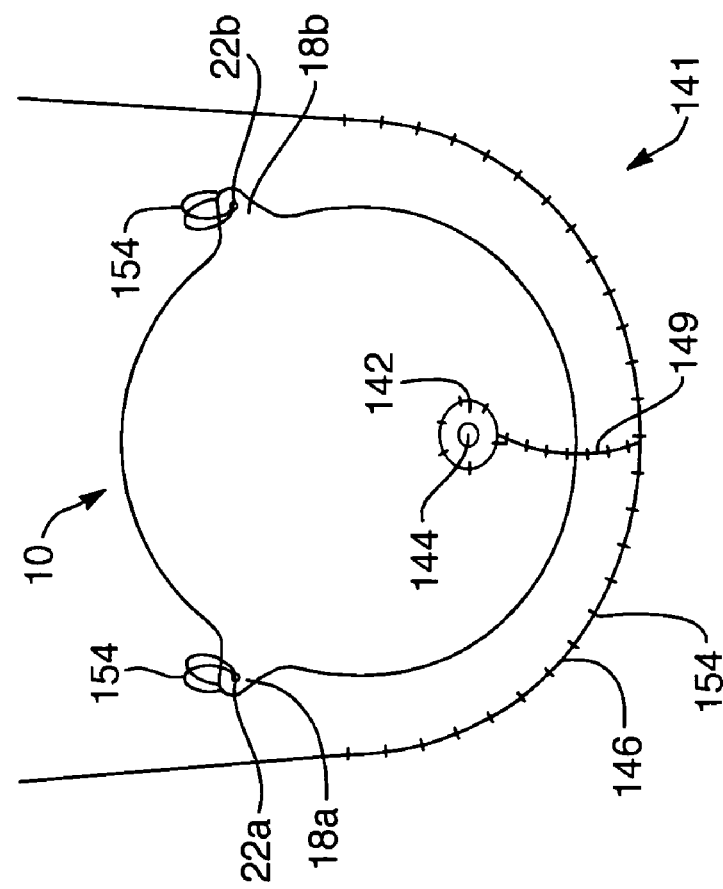
FIG. 22B is a schematic, front elevation view of the anatomy and device of FIG. 22A.
Figure 22A:
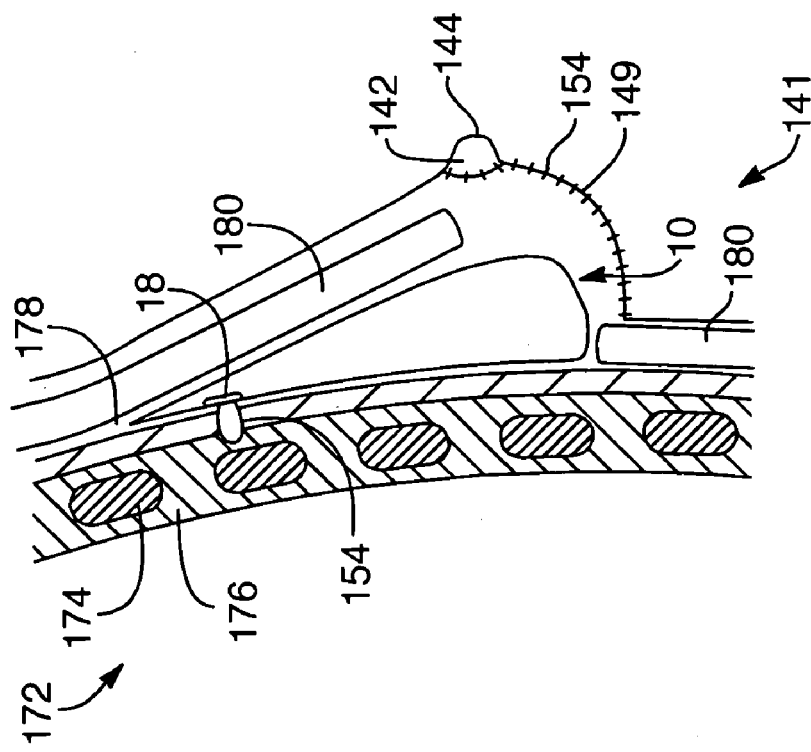
FIG. 22A is a schematic, side elevation, cross-sectional view of an apparatus in accordance with the invention secured by a method in accordance therewith for sub-muscular insertion of an implant in association with a mastopexy procedure.
Figure 22D:
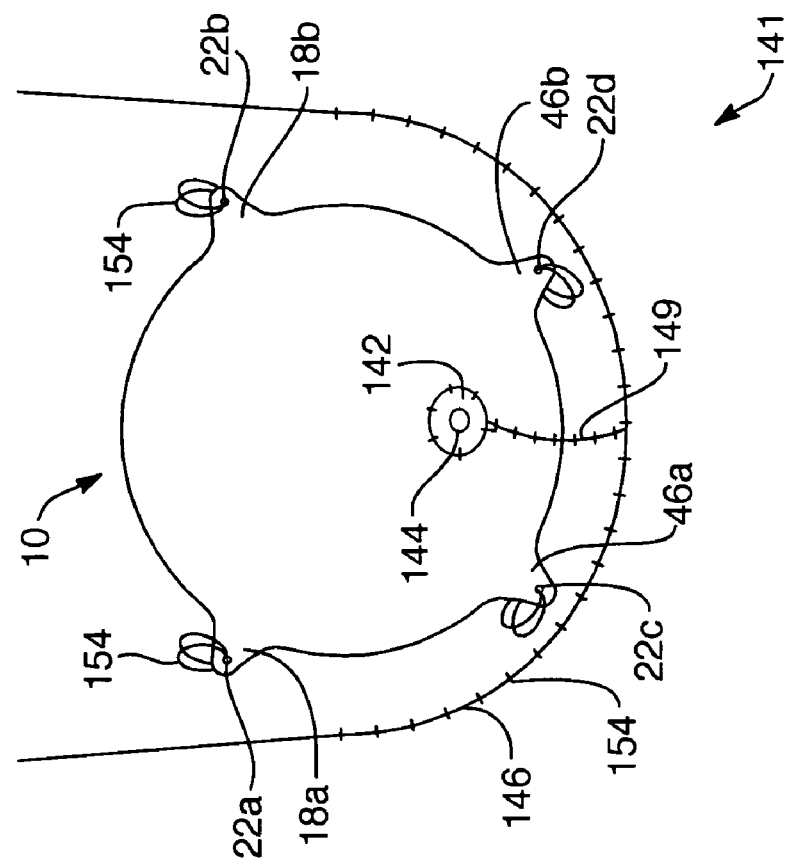
FIG. 22D is a schematic, front elevation view of the system of FIG. 22C, wherein the apparatus of FIGS. 22A–22B include only superiorly mounted, homogeneously formed suture tabs and the apparatus of FIGS. 22C–22D includes both superiorly and inferiorly mounted suture tabs for mastopexy stabilization in accordance with the invention.
Figure 22C:
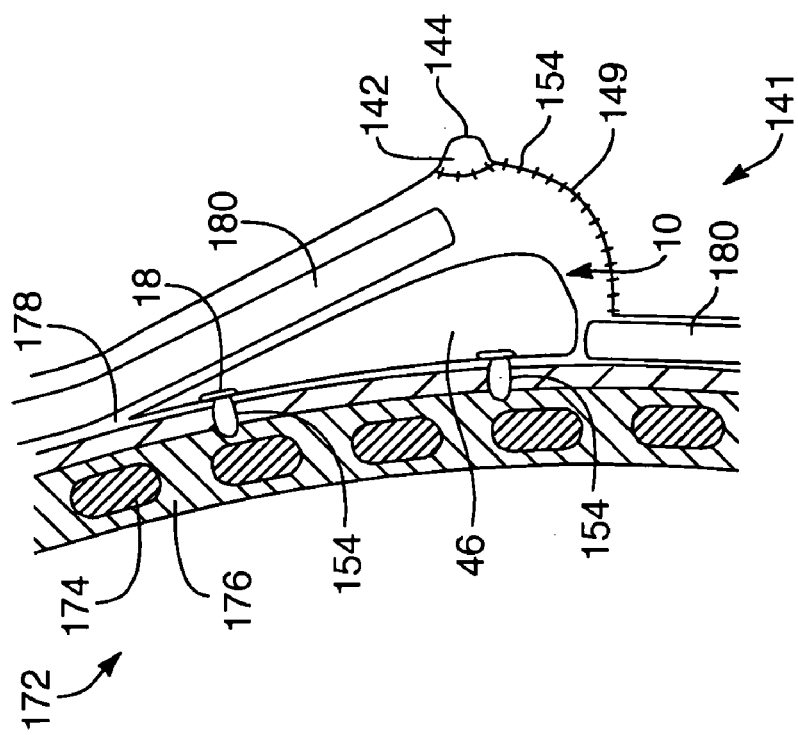
FIG. 22C is a schematic, side elevation, cross-sectional view of the anatomy and device in accordance with the invention, connected by a method in accordance with the invention in a sub-muscular configuration.

Referring to FIG. 20, while continuing to refer generally to FIGS. 1–19, the excised tissue 158 represents both skin and underlying supporting tissue. After removal thereof, a new balance is struck between the mass and volume of contained tissues, and the supporting strength of surrounding skin tissue. Forces may exist along both a superior-inferior axis 160 as well as along a lateral-medial axis 166. Meanwhile, the compressive forces 166 of underlying tissues may be resisted by the tensile forces 168 of the sutures 154.

By the same token, solidus tissues do not flow, but distort quite flexibly. They sometimes behave something like liquids in providing a substantially omnidirectional pressure 170 in response to distortion or pressure. Accordingly, the sutures 154 must resist the pressure 170 imposed by the response of tissues to gravitational forces acting on overlying tissues supported thereby. In prior art systems of implants, the implants themselves add gravitational forces along the axis 160 resulting in pressure 170. The anchoring 115 of the apparatus 10 in accordance with the invention alleviates these loads and reduces internal and external scarring and scar widths along the midline 149 and along the inframammary boundary 146.

Referring to FIGS. 21A–21D, while referring generally to FIGS. 1–20, an apparatus 10 in accordance with the invention may be sutured in one embodiment directly to a muscle 180. The muscle 180 overlies the chest wall 172 comprising both ribs 174 and intervening cartilage 176. The chest wall 172 is protected by a fascia 178 overlying it. In a subglandular positioning of an apparatus 10 in accordance with the invention, the apparatus 10 underlies the mammary gland network and surrounding tissues. However, the apparatus 10 lies outside the muscle 180, and is secured by sutures 154 anchoring the apparatus 10 to the muscle 180.

Referring to FIGS. 22A–22D, while continuing to refer generally to FIGS. 1–21, an apparatus 10 in accordance with the invention may be connected to the wall 172 or chest wall 172 of a patient. Connections to the chest wall 172 may include suture to a rib 174, or cartilage 176 located between ribs. In general, a needle 30 and suture 20 will be passed by a surgeon through the fascia 178 protecting the chest wall 172, penetrate the cartilage 176, or the cartilage 176 and a portion of rib 174, and return out through the fascia 178. Typically, the suture 154 will be made as a series of loops, when anchoring 115. In certain embodiments, the suture 154 may actually progress along a particular path, such as a periphery of the implant 10, and thus involve several stitches distributed along a suture path. In implants applied to other areas of the body, sutures may be similarly located.

In an application as illustrated in FIGS. 22A–22D, the location of the apparatus 10 is sub-muscular. Accordingly, the chest muscle 180 is separated from the fascia 178, in order to position the implant and/or apparatus 10 between the fascia 178 and the muscle 180. Accordingly, the sutures 154 penetrate into the chest wall 172, connecting to either a rib 174, intervening cartilage 176, or both. Accordingly, the suture 154 will typically pass through the fascia 178 and return outside the chest cavity for knotting 124 by the surgeon.

Figure 23:
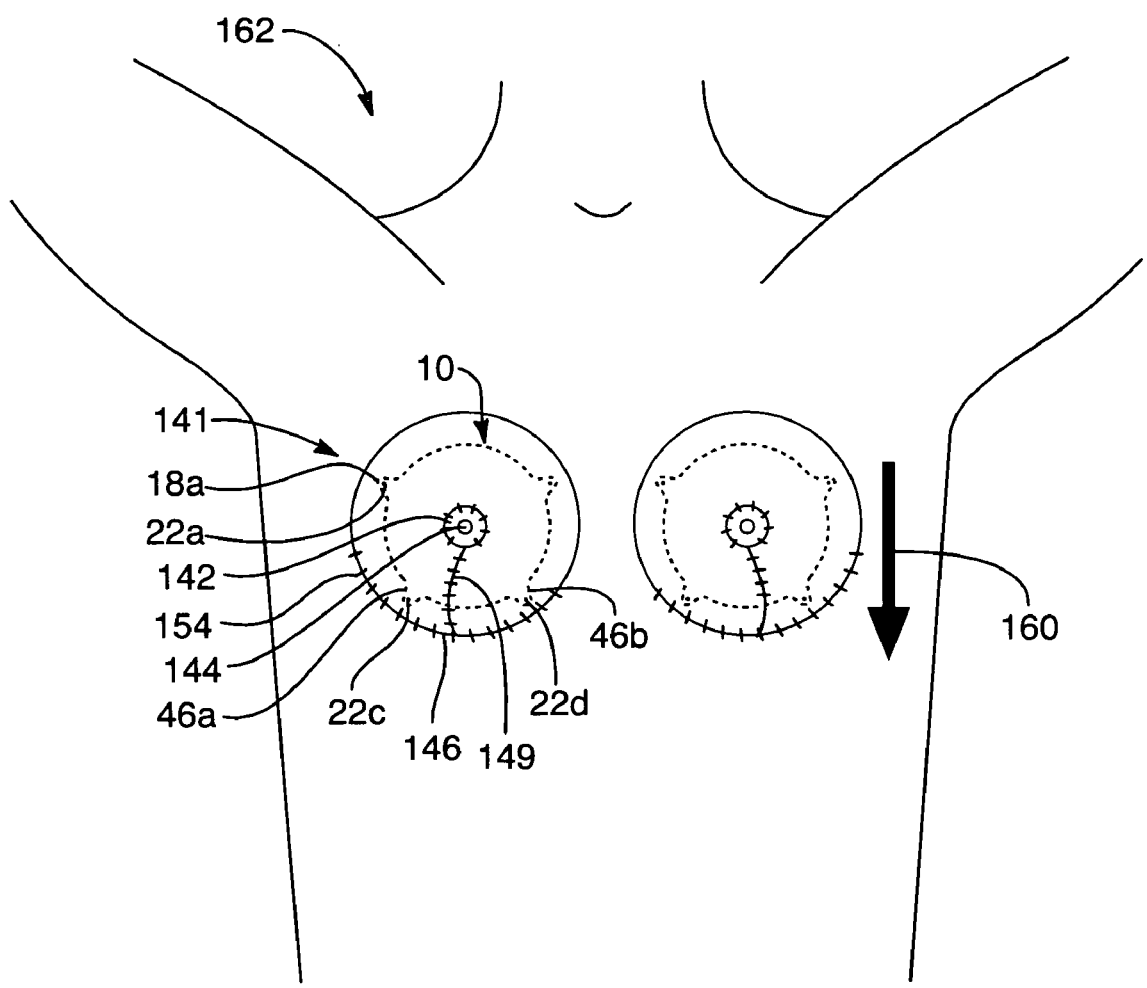
FIG. 23 is a schematic front elevation view of the orientation and load characterization against the suture locations as driven by the weight of implants in accordance with the invention.
Figure 24:
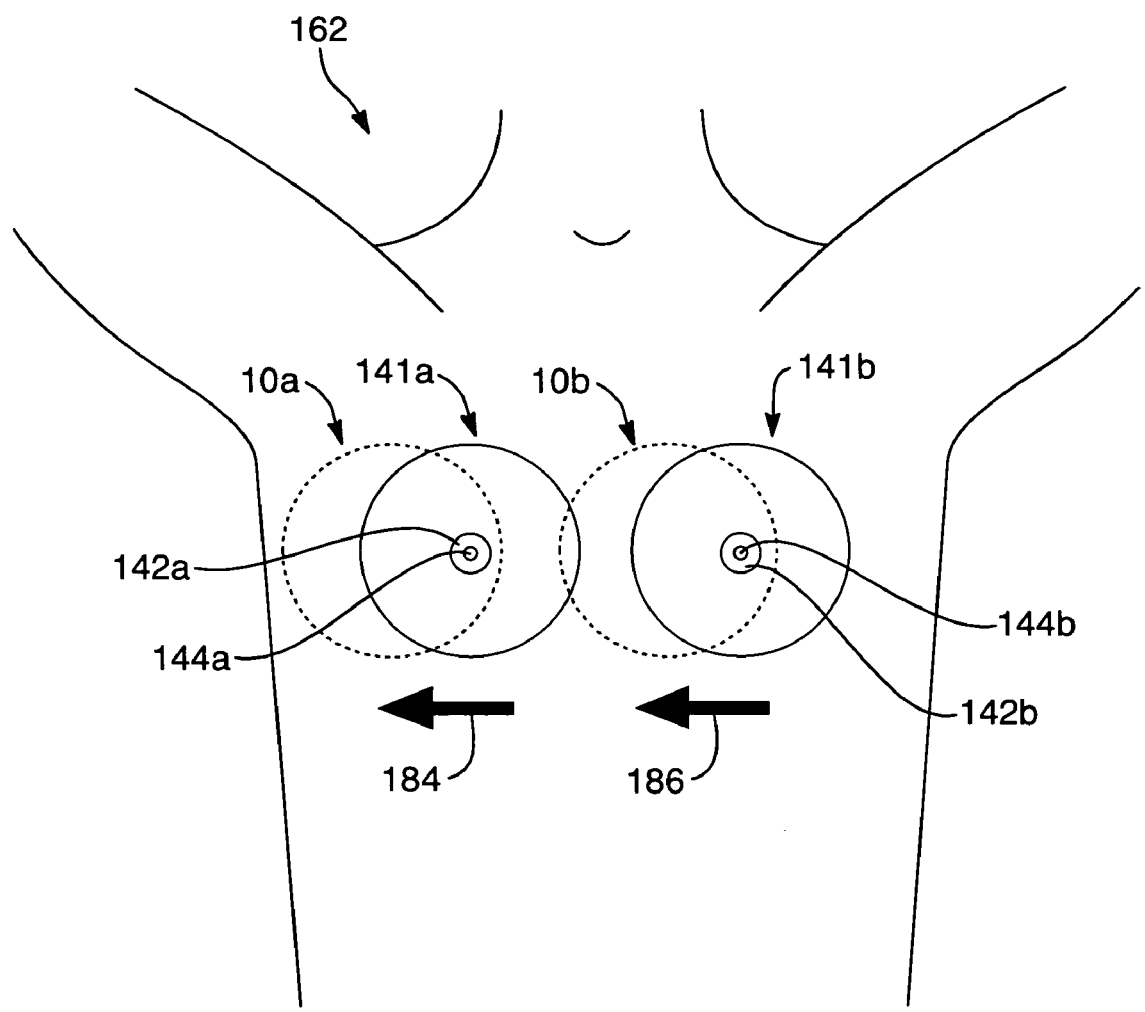
FIG. 24 is a schematic front elevation view of the forces and propensity to or toward lateral and medial displacement of implants to be resisted by a method and apparatus in accordance with the invention.
Figure 25:
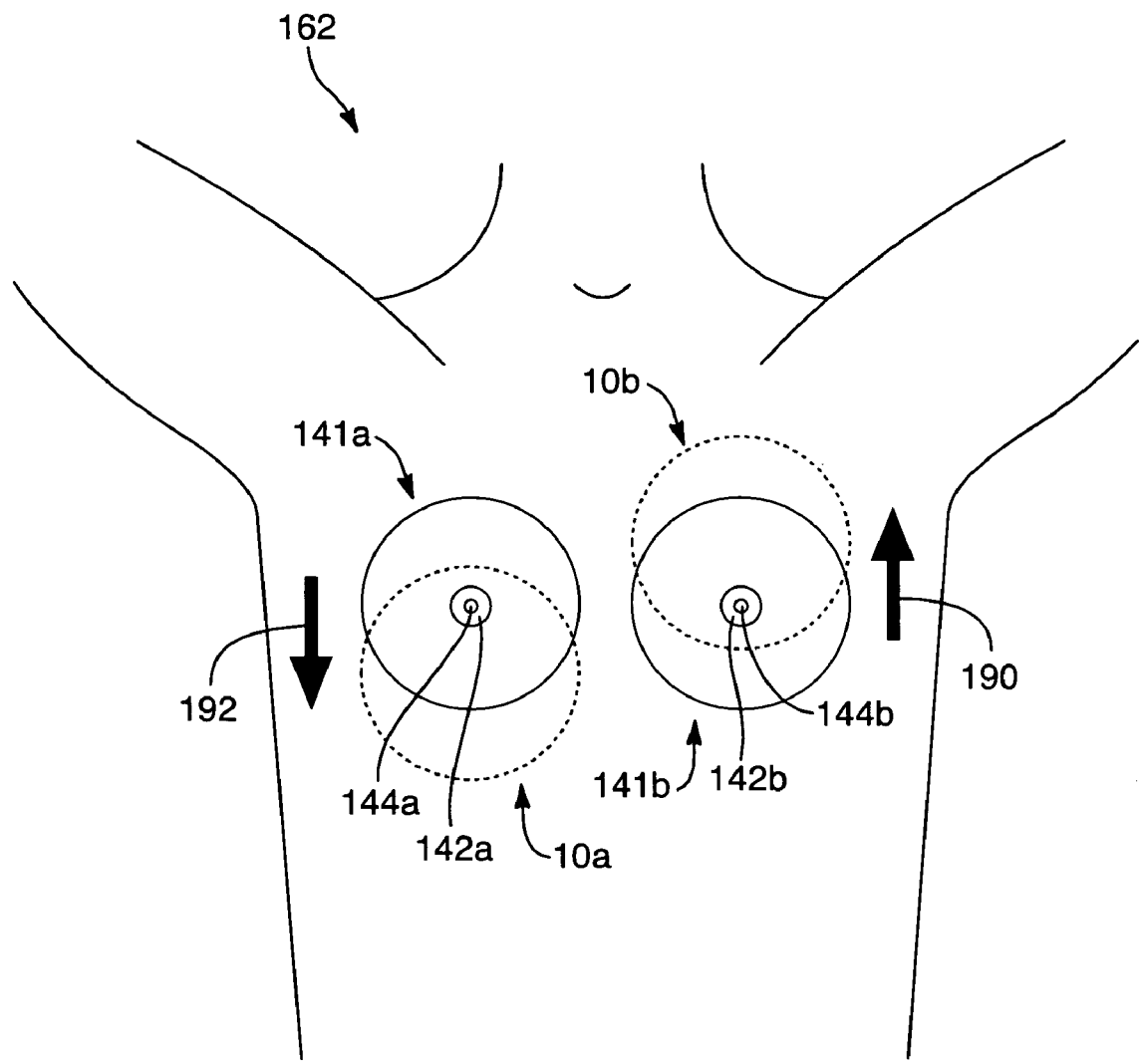
FIG. 25 is a schematic, front elevation view of the forces and propensity toward inferior and superior migration of implants resisted by an apparatus and method in accordance with the invention.

Referring to FIGS. 23–25, the forces 160 associated with gravitational acceleration of all masses, are not resisted by skeletal structure. Accordingly, the soft tissues associated with a mastopexy operation may be subject to distortion, displacement, stretching, and the like in response to the forces 160 of gravity, and resulting omnidirectional pressures from tissues. Accordingly, the anchoring 115 of the apparatus 10 to the body in a subglandular or submuscular application can resist the displacement in response to the forces 160.

Referring to FIG. 24, strenuous activities, sports, movement while sleeping, forces, pressure, and the like that naturally occur with the body, may affect the apparatus 10 differently from surrounding tissues. Accordingly, tissues may rupture, inflame, stretch, or otherwise permit migration of the apparatus 10 absent suitable anchoring 115. Accordingly, to provide stability against rotation around substantially any axis, as well as resistance to lateral displacement 184 (laterally toward outside the rib cage and under the arm) may be resisted by the apparatus 10 in according with the invention. Similarly, medial displacement 186 toward the sternum and away from the underarm area may be avoided.

Either displacement 184, 186 by an implant 10 or apparatus 10 in accordance with the invention may produce asymmetry and distortion undesirable in a patient. The forces 184, 186 may result from athletic activity, contact with objects or persons, or other influences that may produce a force that tissues will respond to locally. A foreign object such as the apparatus 10 may respond more monolithically to forces 184, 186. Accordingly, distortions in response to forces 184, 186 are resisted in an apparatus 10 in accordance with the invention.

Referring to FIG. 25, forces 190, 192 in the superior and inferior directions, respectively, may operate similarly to those of FIG. 24. In the absence of anchoring 115, forces occurring during athletic activity or contact with objects or persons, as well as natural reactions of tissues, and the like may result in either superior or inferior displacement in the absence of anchoring 115.

Figure 26A:
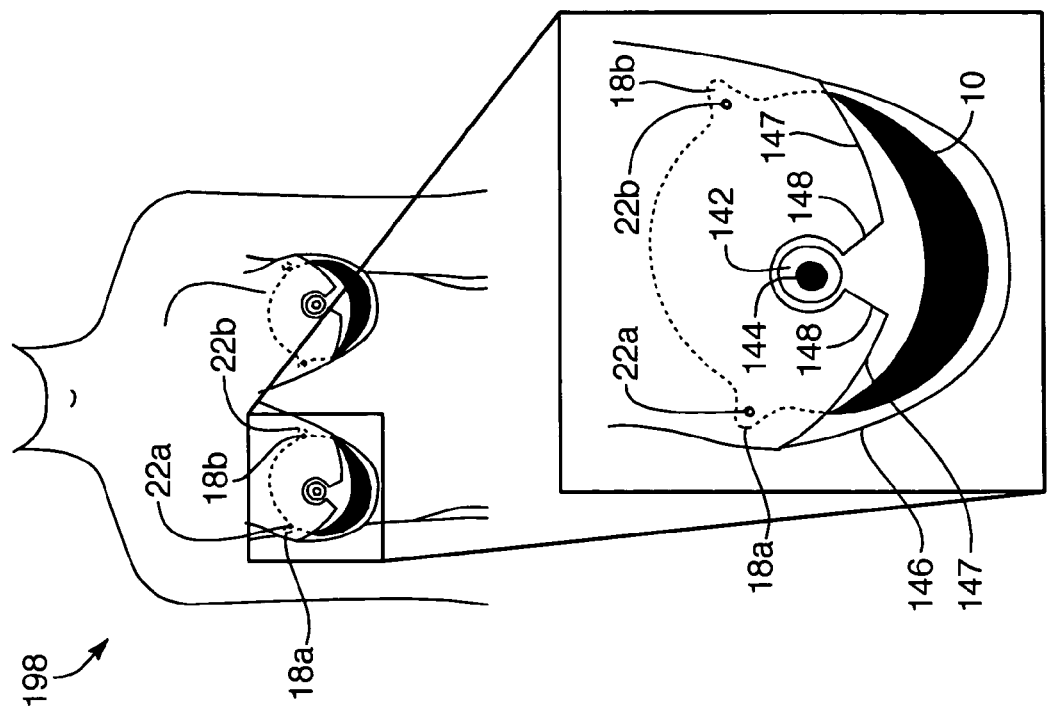
FIG. 26A is a schematic front elevation view of the region of tissue to be incised and excised in a mastopexy in accordance with the invention.
Figure 26B:
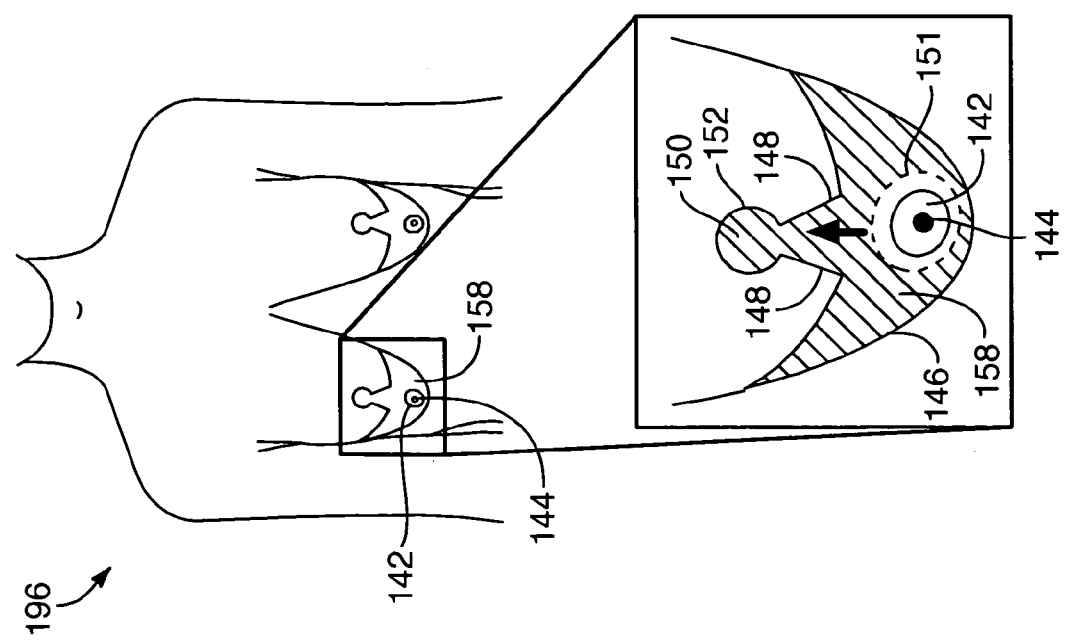
FIG. 26B is a schematic front elevation view of insertion of an apparatus in accordance with the invention prior to closure of incisions, and after excision of removed materials.

Referring to FIG. 26, a ptosis condition 198 is illustrated in FIG. 26A, along with the demarcation lines that will be the subject of the incisions described with respect to FIGS. 19–22. Referring to FIG. 26B, the process 90 in accordance with the invention is illustrated showing the incisions along which openings will be formed, and the pocket formed, as well as the incisions that will be closed after excision of excess tissues.

Figure 27:
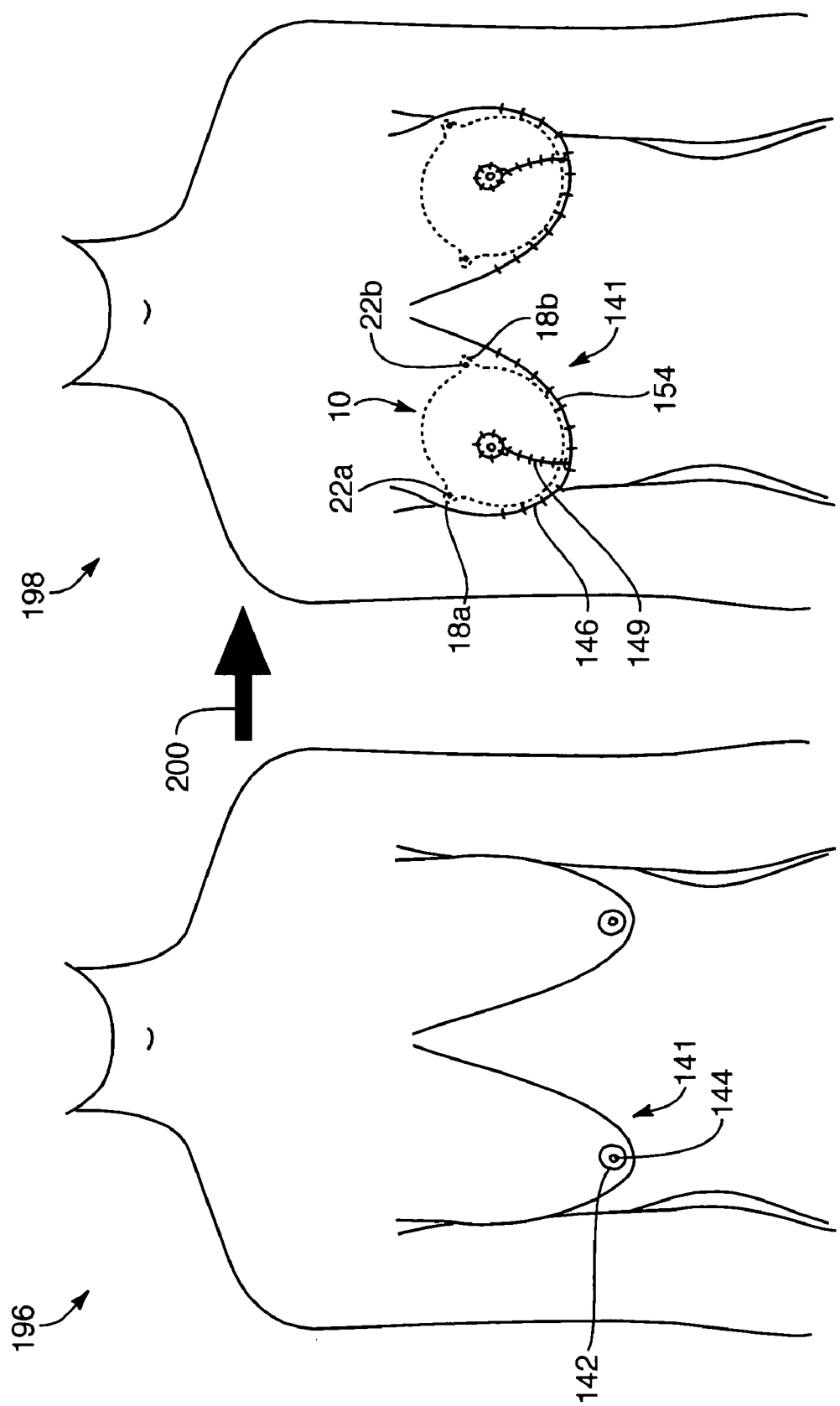
FIG. 27 is a schematic front elevation view of the transformation in accordance with an apparatus and method of the invention from a ptosis condition to a lifted and augmented condition.

Referring to FIG. 27, the ptosis condition 196 is shown transformed 200 by the process 100 to a lifted condition 198 as illustrated. Thus, it can be seen that an apparatus and method in accordance with the invention provide for an improved apparatus 10 to be used in an improved process 100 for correcting a ptosis condition 196.

From the above discussion, it will be appreciated that the present invention may be embodied in other specific forms without departing from its essential characteristics. The described embodiments are to be considered in all respects only as illustrative, and not restrictive. The scope of the invention is, therefore, indicated by the appended claims, rather than by the foregoing description. All changes within the meaning and range of equivalency of the claims are to be embraced within their scope.

What is claimed as new and desired by Letters Patent of the United States is:

1. An apparatus for mastopexy with augmentation, the apparatus comprising:
   a vessel of an elastomeric material shaped as an outer covering of predetermined form and size to provide augmentation in a mastopexy procedure;
   a filler to maintain a volume of the vessel;
   the vessel, further comprising a back wall forming a surface for contact with tissue posterior thereto;
   a plurality of anchors, each anchor comprising a suture embedded within and to extend along the back wall and terminating at a first end spaced away from the back wall; and
   a surgical needle connected to draw the first end of at least one anchor of the plurality of anchors.

2. The apparatus of claim 1, wherein the filler is selected from the group consisting of water, saline, silicone, silicone gel, sugar, hydrogel, and a combination of two or more thereof.

3. The apparatus of claim 1, further comprising a protective covering surrounding the surgical needle to resist inadvertent puncture of the vessel.

4. The apparatus of claim 1, wherein the elastomeric material is selected from the group consisting of a polymer, a reinforced polymer, an expanded polymer, and a combination of at least two thereof.

5. The apparatus of claim 4, wherein the elastomeric material is a polymer.

6. The apparatus of claim 5, wherein the polymer is a silicone compound.

7. The apparatus of claim 6, wherein the silicone compound is dimethylsiloxane.

8. The apparatus of claim 4 wherein the back wall comprises at least one embedded fiber.

9. The apparatus of claim 8, wherein at least two embedded fibers cross one another.

10. The apparatus of claim 9, wherein the at least two fibers cross at substantially a right angle.

11. The apparatus of claim 9, wherein the at least two fibers cross at an acute angle.

12. The apparatus of claim 8, wherein the at least one embedded fiber runs in substantially a superior-inferior direction.

13. The apparatus of claim 8, wherein the at least one embedded fiber runs in a substantially medial-lateral direction.

14. The apparatus of claim 8, wherein the at least one embedded fiber extends diagonally with respect to a medial-lateral direction and a superior-inferior direction.

15. The apparatus of claim 1, wherein the plurality of anchors comprises a first anchor extending substantially radially from the back wall in the direction of about the ten o'clock position and a second anchor extending substantially radially from the back wall in the direction of at about the two o'clock position.

16. The apparatus of claim 1, wherein the back wall is substantially circular and absent tabs extending outwardly therefrom.

17. An apparatus for mastopexy with augmentation, the apparatus comprising:
   a vessel of an elastomeric material of predetermined form and size to provide augmentation in a mastopexy procedure, the vessel including a back wall for contact with tissue posterior thereto;
   a filler to maintain a volume of the vessel;
   a plurality of anchors, each anchor thereof comprising a suture embedded within the back wall and terminating at a first end extending outwardly from the back wall of the vessel; and
   a surgical needle connected to draw the first end of at least one anchor of the plurality of anchors.

18. An apparatus for mastopexy with augmentation, the apparatus comprising:
   a vessel comprising at least one wall formed of an elastomeric material to support augmentation through a mastopexy procedure;
   a filler placed within the vessel to maintain a volume thereof; and
   a plurality of sutures securing to the vessel substantially exclusively through embedment within the at least one wall and terminating at respective first ends extending outwardly from the at least one wall.

19. The apparatus of claim 17, wherein the back wall is substantially circular and absent protrusions thereof extending outwardly.

20. The apparatus of claim 19, further comprising a protective covering surrounding the surgical needle to resist inadvertent puncture of the vessel.

21. The apparatus of claim 18, wherein the back wall is substantially circular, without tabs extending outwardly therefrom.

* * * * *